(12) United States Patent
Hanada

(10) Patent No.: US 9,173,968 B2
(45) Date of Patent: Nov. 3, 2015

(54) STERILIZATION APPARATUS AND STERILIZATION METHOD

(71) Applicants: CANON MARKETING JAPAN KABUSHIKI KAISHA, Tokyo (JP); ELK CORPORATION, Osaka (JP); KABUSHIKI KAISHA ELQUEST, Chiba (JP)

(72) Inventor: Yasushi Hanada, Chiba (JP)

(73) Assignees: CANON MARKETING JAPAN KABUSHIKI KAISHA, Tokyo (JP); KABUSHIKI KAISHA ELQUEST, Chiba (JP); ELK CORPORATION, Osaka (JP)

(*) Notice: Subject to any disclaimer, the term of this patent is extended or adjusted under 35 U.S.C. 154(b) by 63 days.

(21) Appl. No.: 13/645,194

(22) Filed: Oct. 4, 2012

(65) Prior Publication Data

US 2013/0089462 A1    Apr. 11, 2013

(30) Foreign Application Priority Data

Oct. 6, 2011 (JP) ................................. 2011-222382
Oct. 31, 2011 (JP) ................................. 2011-239562

(51) Int. Cl.
*A61L 2/20* (2006.01)

(52) U.S. Cl.
CPC ...................................... *A61L 2/208* (2013.01)

(58) Field of Classification Search
CPC ........................................................ A61L 2/208
USPC ............................................. 422/33, 292, 300
See application file for complete search history.

(56) References Cited

U.S. PATENT DOCUMENTS 5,348,711 A * 9/1994 Johnson et al. ............... 422/300

FOREIGN PATENT DOCUMENTS

JP    2009-501631 A    1/2009

* cited by examiner

*Primary Examiner* — Sean E Conley
(74) *Attorney, Agent, or Firm* — Canon USA, Inc. IP Division

(57) ABSTRACT

There is provided a sterilization apparatus for sterilizing an object. The sterilization apparatus includes a concentration chamber configured to concentrate sterilizer, a vaporizing chamber configured to vaporize the sterilizer, a measuring pipe into which the sterilizer is introduced from the concentration chamber before being introduced into the vaporizing chamber, a vacuuming device configured to vacuum the sterilization chamber, and a first valve configured to be opened and closed to control communication between the sterilization chamber and the measuring pipe, wherein after the sterilizer is introduced from the concentration chamber into the measuring pipe, gas contained in the measuring pipe is removed from the measuring pipe by opening the first valve.

10 Claims, 18 Drawing Sheets

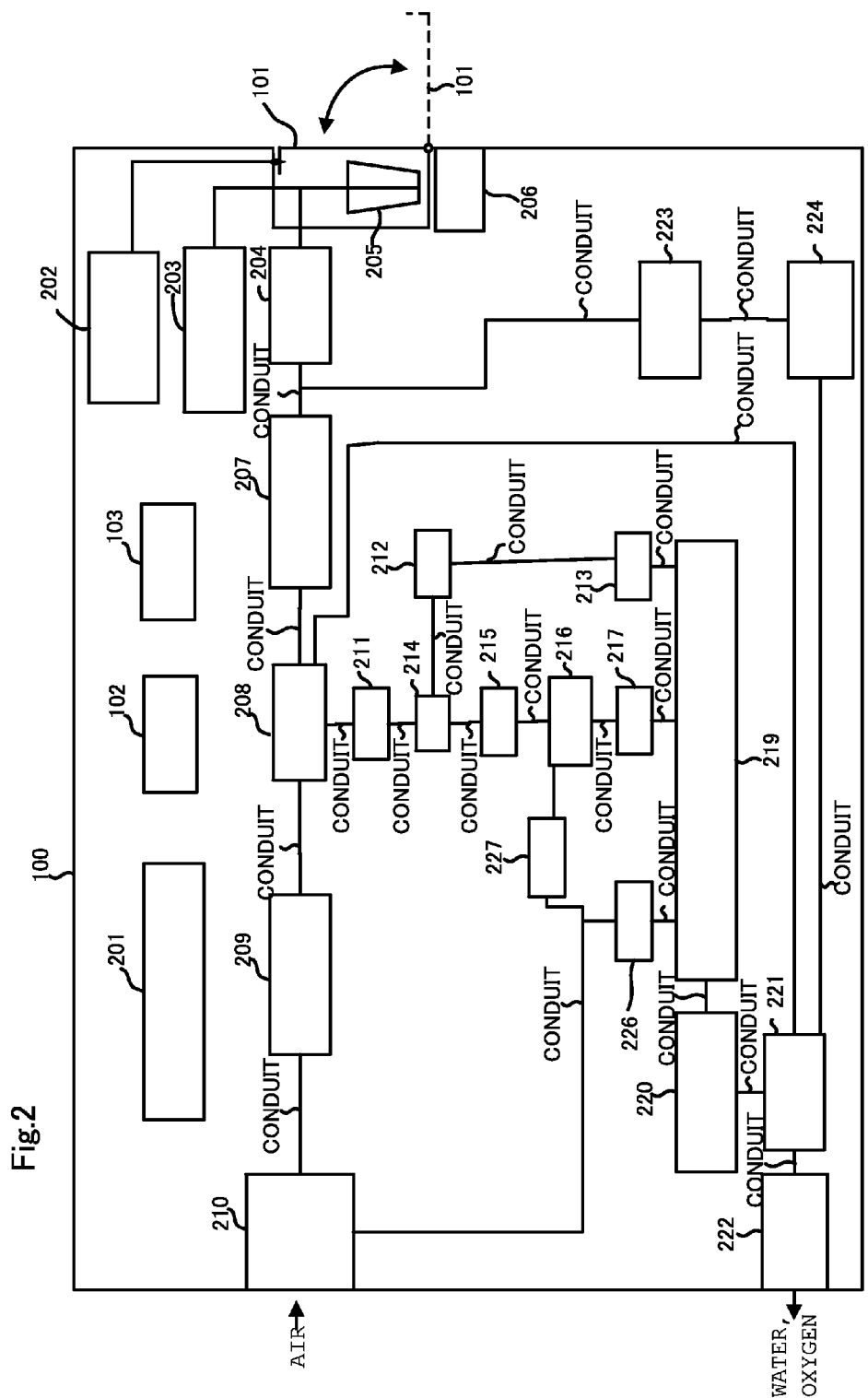

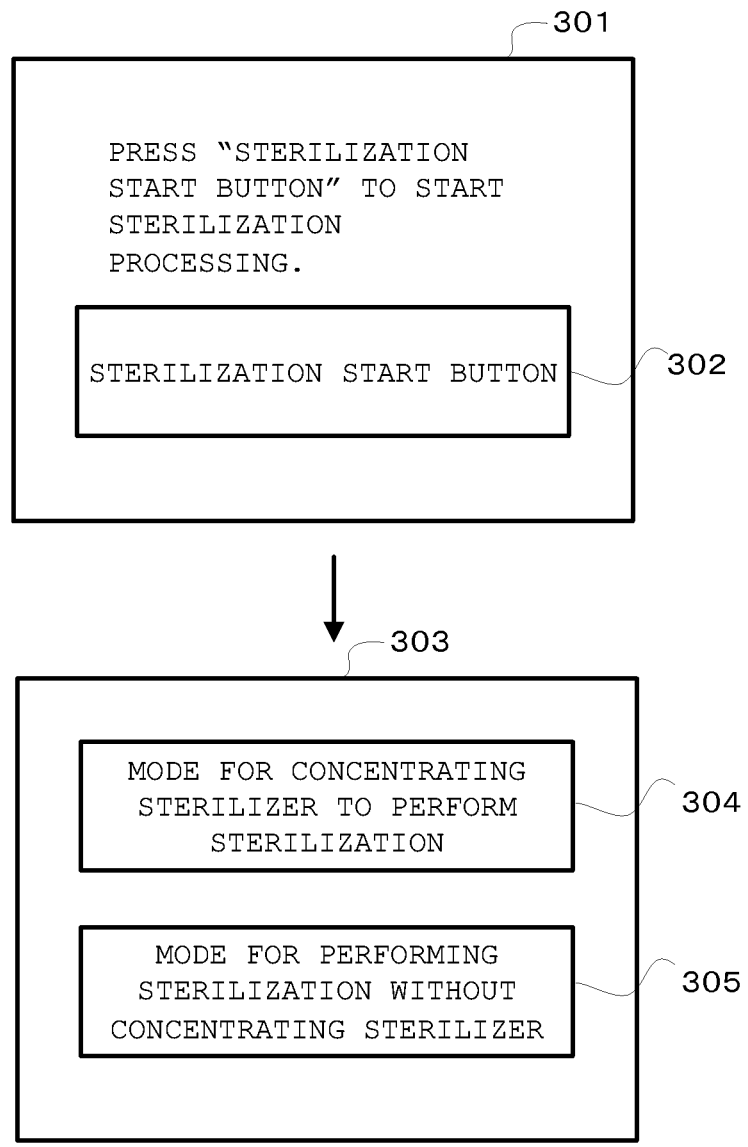

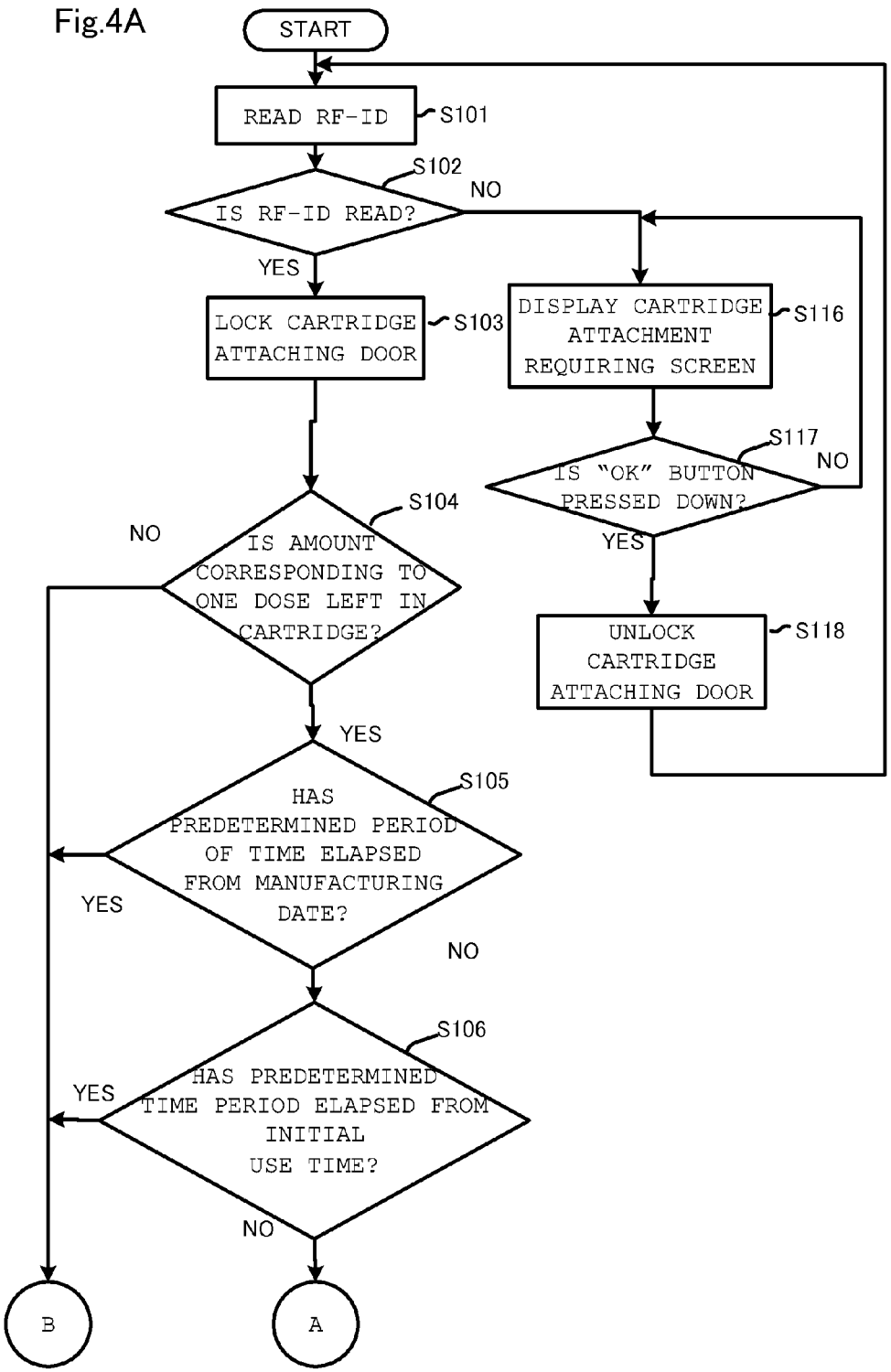

STERILIZATION APPARATUS AND STERILIZATION METHOD

BACKGROUND OF THE INVENTION

1. Field of the Invention

One disclosed aspect of the embodiments relates to a sterilization apparatus and a sterilization method.

2. Description of the Related Art

Because germs may be attached to medical instruments such as syringes or operation tools if the medical instruments are not sterilized after used, the medical instruments may badly influence human bodies and thus may not be reused. For this reason, sterilization apparatuses for sterilizing an object, such as a medical instrument, which needs to be sterilized, are being used.

As an example of such a sterilization apparatus and a sterilization method, which sterilize an object by using hydrogen peroxide as a sterilizer are discussed, for example, in Japanese Unexamined Patent Application Publication (Translation of PCT Application) No. 08-505787.

When a sterilization object is sterilized by a sterilization apparatus, a sterilizer is concentrated in a concentration furnace, and sterilization is performed by using the concentrated sterilizer to increase a sterilizing operation. While the sterilizer concentrated in the concentration furnace passes through a chamber for gasifying the concentrated sterilizer from the concentration furnace, air in a cartridge used a plurality of times or air for exhausting vapor is mixed.

For this reason, if air is introduced into a sterilization chamber, a sterilizing operation is deteriorated.

SUMMARY OF THE INVENTION

One disclosed aspect of the embodiments is directed to a sterilization apparatus and a sterilization method capable of preventing air from entering into a sterilization chamber.

One disclosed feature of the embodiments may be described as a process which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a program, a procedure, a method of manufacturing or fabrication, etc. One embodiment may be described by a schematic drawing depicting a physical structure. It is understood that the schematic drawing illustrates the basic concept and may not be scaled or depict the structure in exact proportions.

According to an aspect of the embodiments, a sterilization apparatus includes a concentration chamber configured to concentrate sterilizer, a vaporizing chamber configured to vaporize the sterilizer, a measuring pipe into which the sterilizer is introduced from the concentration chamber before being introduced into the vaporizing chamber, a vacuuming device configured to vacuum the sterilization chamber, and a first valve configured to be opened and closed to control communication between the sterilization chamber and the measuring pipe, wherein after the sterilizer is introduced from the concentration chamber into the measuring pipe, gas contained in the measuring pipe is removed from the measuring pipe by opening the first valve.

According to another aspect of the embodiments, a sterilization method in a sterilization apparatus for sterilizing an object including a concentration chamber configured to concentrate a sterilizer, a vaporizing chamber configured to vaporize the sterilizer, a measuring pipe into which the sterilizer is introduced from the concentration chamber before introduced into the vaporizing chamber, a vacuuming device configured to vacuum the sterilization chamber, and a first valve configured to be opened and closed to control communication between the sterilization chamber and the measuring pipe, includes removing gas contained in the measuring pipe from the measuring pipe by opening the first valve, after the sterilizer is introduced from the concentration chamber into the measuring pipe.

Further features and aspects of the disclosure will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the disclosure and, together with the description, serve to explain the principles of the disclosure.

FIG. 2 is a block diagram illustrating an example of a hardware configuration of the sterilization apparatus according to an exemplary embodiment.

FIG. 3 is a diagram illustrating an example of a screen displayed on a display unit 102 of the sterilization apparatus 100.

FIG. 4A is the first part of a flowchart illustrating an example of processes of a sterilization processing by the sterilization apparatus according to an exemplary embodiment.

DESCRIPTION OF THE EMBODIMENTS

Various exemplary embodiments, features, and aspects of the disclosure will be described in detail below with reference to the drawings.

Hereinafter, a sterilization apparatus according to a first exemplary embodiment will be described with reference to the accompanying drawings. First, an appearance of the sterilization apparatus according to the present exemplary embodiment will be described with reference to FIG. 1.

Figure 1:
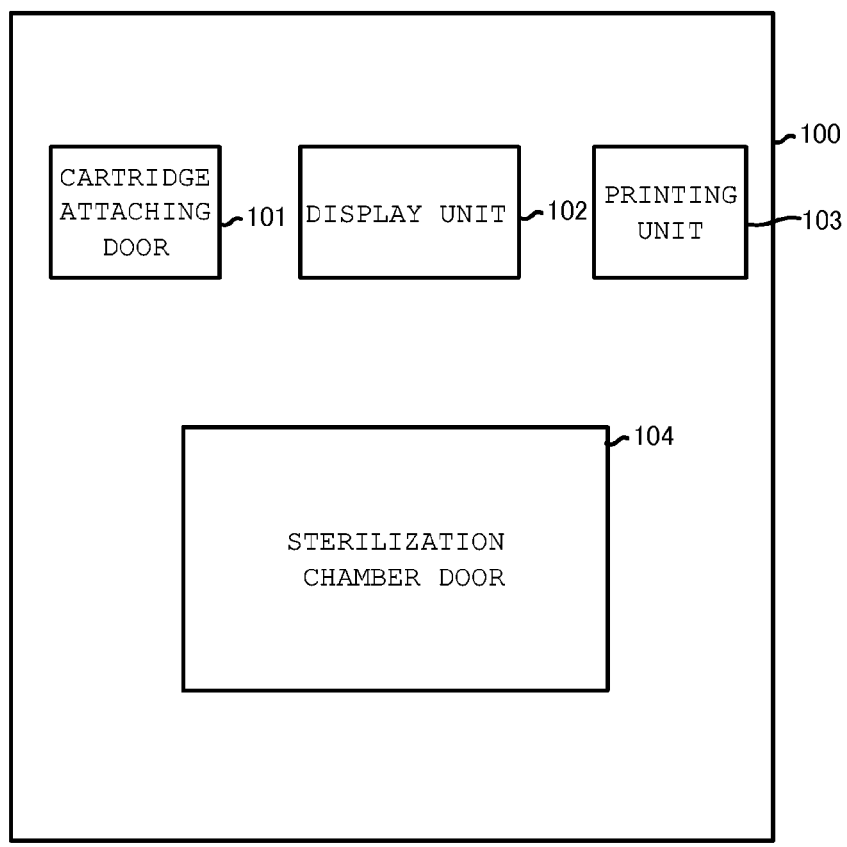
FIG. 1 is a diagram illustrating an appearance of a sterilization apparatus according to an exemplary embodiment viewed from the front side.

FIG. 1 is a diagram illustrating an appearance of a sterilization apparatus according to the present exemplary embodiment viewed from the front side. A sterilization apparatus 100 includes a cartridge attaching door 101, a display unit 102, a printing unit 103, and a sterilization chamber door 104.

The cartridge attaching door 101 is a door used for attaching a cartridge, which is a container where a sterilizer (hydrogen peroxide or a hydrogen peroxide solution liquid) is filled. If the cartridge attaching door 101 is opened, a cartridge attaching position is viewed and a user may attach the cartridge thereto.

The display unit 102 is a display screen of a touch panel such as a liquid crystal monitor. The printing unit 103 is a printer for printing a sterilization history or a sterilization result on a printing sheet, and properly prints a sterilization history or a sterilization result on a printing sheet.

The sterilization chamber door 104 is a door for inserting, for example, a sterilization target (sterilization object) such as medical instruments into the sterilization chamber to sterilize the sterilization object. If the sterilization chamber door 104 is opened, the sterilization chamber is viewed, and the sterilization object is placed in the sterilization chamber, and then the sterilization chamber door 104 is closed. Thus, the sterilization target may be placed in the sterilization chamber.

The sterilization chamber is a casing having a predetermined capacity. The pressure in the sterilization chamber may be maintained at a pressure from the atmospheric pressure to a vacuum pressure. Further, the temperature in the sterilization chamber is maintained at a temperature within a predetermined range during a sterilization processing.

Next, an example of a hardware configuration of the sterilization apparatus according to the present exemplary embodiment will be described with reference to FIG. 2. FIG. 2 is a diagram illustrating an example of a hardware configuration of a sterilization apparatus according to the present exemplary embodiment.

The sterilization apparatus 100 according to the present exemplary embodiment includes an operation processing unit (e.g., MPU) 201, a display unit 102, a printing unit 103, a lock operation control unit 202, an extraction needle operation control unit 203, a cartridge attaching door 101, a liquid sensor 204, a cartridge 205, an RF-ID reader/writer 206, a liquid feeding rotary pump 207, a concentration furnace 208, a gas feeding pressing pump 209, a gas suctioning HEPA filter 210, a valve (V1) 211, a valve (V3) 212, a valve (V4) 213, a measuring pipe 214, a valve (V2) 215, a vaporizing furnace 216, a valve (V5) 217, a valve (V9) 227, a valve (V7) 226, a sterilization chamber (also referred to as a vacuum chamber) 219, a gas feeding vacuum pump 220, a gas exhausting HEPA filter 221, a sterilizer decomposing unit 222, a liquid feeding rotary pump 223, and a gas exhausting/evaporating furnace 224.

The sterilization apparatus 100 is an apparatus for extracting a sterilizer from the cartridge 205, which stores the sterilizer, to sterilize an object. The operation processing unit 201 performs calculation processing and controls various components of the hardware constituting the sterilization apparatus 100. The display unit 102, the printing unit 103, and the cartridge attaching door 101 have already been described with reference to FIG. 1, and thus a detailed description thereof will be omitted.

The lock operation control unit 202 is a unit for performing a locking/unlocking operation of the cartridge attaching door 101, and by locking the cartridge attaching door 101, the cartridge attaching door 101 may be prevented from being opened, and by unlocking the cartridge attaching door 101, the cartridge attaching door 101 is allowed to be opened.

The cartridge 205 is a sealed container in which a sterilizer (hydrogen peroxide or a hydrogen peroxide solution) is filled. Further, an RF-ID storage medium is disposed at a lower side of the cartridge 205, and the storage medium stores, as information for identifying the cartridge, a serial number, a manufacturing date of the cartridge, a date and time (initial use date and time) when the cartridge is used in the sterilization apparatus for the first time, and a residual amount of the sterilizer filled in the cartridge.

The RF-ID is a storage medium storing data (data on all or any one of a serial number, a manufacturing date, an initial use date and time, and a residual amount of a sterilizer) relating to waste of the sterilizer in the cartridge 205. The extraction needle operation control unit 203 is a unit for operating an extraction needle (syringe needle) for suctioning the sterilizer in the cartridge to prick the extraction needle from the upper portion of the cartridge.

That is, when the extraction needle (syringe needle) for suctioning the sterilizer in the cartridge is pricked from an upper portion of the cartridge, the extraction needle (syringe needle) may be pricked from the upper portion of the cartridge by operating the extraction needle (syringe needle) to be lowered toward the cartridge from the upper portion of the cartridge. Further, when the extraction needle (syringe needle) is withdrawn from the cartridge, the extraction needle (syringe needle) may be withdrawn from the cartridge by operating the extraction needle to be raised from an upper portion of the cartridge.

The extraction needle is a straw (thin tube) for suctioning the sterilizer in the cartridge. The liquid sensor 204 is a unit for detecting whether the liquid sterilizer in the cartridge 205 is passing through the liquid feeding rotary pump 207 and a pipe (conduit) communicated (connected) with the liquid feeding rotary pump 223 from the extraction needle (syringe needle). More specifically, it may be detected, from a spectrum obtained by irradiating an infrared ray to the pipe, whether the sterilizer is passing through the pipe.

The RF-ID reader/writer 206 is a unit for reading a serial number, a manufacturing date, an initial use date and time, and a residual amount of a sterilizer from an RF-ID disposed at a lower side of the cartridge 205. Further, the RF-ID reader/writer 206 is a unit for writing an initial use date and time and a residual amount of a sterilizer in the RF-ID disposed on the lower side of the cartridge 205.

Further, the RF-ID reader/writer 206 is disposed at a lower portion of a cartridge attaching position located behind the cartridge attaching door 101, and may read the RF-ID disposed on the lower side of the cartridge 205, and record data such as an initial use date and time, a residual amount of a sterilizer, and the like in the RF-ID.

The liquid feeding rotary pump 207 is communicated (connected) with the concentration furnace 208 through a conduit, and is communicated with the liquid sensor 204 through a conduit. The liquid feeding rotary pump 207 is a unit for suctioning the liquid sterilizer in the cartridge 205 with a pump and sending the sterilizer to the concentration furnace 208 through a conduit. Further, the liquid feeding rotary pump 207 may suction a predetermined amount of a sterilizer from the cartridge 205 in cooperation with the liquid sensor 204.

The concentration furnace 208 is communicated with the liquid feeding rotary pump 207, the gas feeding pressing pump 209, the measuring pipe 214, and the gas exhausting HEPA filter 221 through conduits, respectively. The concentration furnace 208 heats the sterilizer carried through a conduit from the liquid feeding rotary pump 207 by using a heater, and evaporates (vaporizes) moisture and the like contained in the sterilizer and concentrates the sterilizer, which will be also described below with reference to FIG. 10 below.

Further, the vaporized water is forced out to a conduit communicated with the gas exhausting HEPA filter 221 by the air carried through a conduit from the gas feeding pressing pump 209, and is exhausted from the concentration furnace 208. In addition, a valve (V1) 211 is disposed in a conduit between the measuring pipe 214 and the concentration furnace 208.

The gas feeding pressing pump 209 is communicated with the concentration furnace 208 and the gas suctioning HEPA filter 210 through conduits, respectively. The gas feeding pressing pump 209 is a unit for sending exterior gas (air) of the sterilization apparatus 100 to the concentration furnace 208 communicated with the gas suctioning HEPA filter 210 through a conduit via the gas suctioning HEPA filter 210.

The gas suctioning HEPA filter 210 is communicated with the gas feeding pressing pump 209, the sterilization chamber 219, and the vaporizing furnace 216 through conduits, respectively. The gas suctioning HEPA filter 210 filters dust, fine dust, and germs in the exterior gas (air) outside the sterilization apparatus 100 with a high efficiency particulate air filter (HEPA filter) to clean air. Further, the cleaned air is sent to the concentration furnace 208 through a conduit by the gas feeding pressing pump 209.

Further, the cleaned air is carried into the vaporizing furnace 216 through a conduit communicated with the vaporizing furnace 216, or is carried into the sterilization chamber 219 through a conduit communicated with the sterilization chamber 219. That is, the gas suctioning HEAP filter 210 is communicated with the exterior gas (air) outside the sterilization apparatus 100. Accordingly, a conduit between the gas feeding pressing pump 209 and the gas suctioning HEPA filter 210, a conduit between the sterilization chamber 219 and the gas suctioning HEPA filter 210, and a conduit between the vaporizing furnace 216 and the gas suctioning HEPA filter 210 are communicated with the exterior gas (air) via the gas suctioning HEPA filter 210.

Further, a valve (V9) 227 is disposed in a conduit between the gas suctioning HEPA filter 210 and the vaporizing furnace 216. In addition, a valve (V7) 226 is disposed in a conduit between the gas suctioning HEPA filter 210 and the sterilization chamber 219.

The valve (V1) 211 is a valve disposed in a conduit between the concentration furnace 208 and the measuring pipe 214, and is a valve configured so that the concentration furnace 208 and the measuring pipe 214 are communicated with each other through the conduit by opening the valve, and the concentration furnace 208 and the measuring pipe 214 are prevented from being communicated with each other through the conduit by closing the valve.

The valve (V3) 212 is a valve disposed in a conduit between the measuring pipe 214 and the sterilization chamber 219, and is a valve configured so that the measuring pipe 214 and the sterilization chamber 219 are communicated with each other through the conduit by opening the valve, and the measuring pipe 214 and the sterilization chamber 219 are prevented from being communicated with each other through the conduit by closing the valve. Further, the valve is disposed around the measuring pipe 214, and is disposed at a location closer to the measuring pipe 214 than at least the below-described valve V4.

The valve (V4) 213 is a valve disposed in a conduit between the measuring pipe 214 and the sterilization chamber 219, and is a valve configured so that the measuring pipe 214 and the sterilization chamber 219 are communicated with each other through the conduit by opening the valve, and the measuring pipe 214 and the sterilization chamber 219 are prevented from being communicated with each other through the conduit by closing the valve. Further, the valve is disposed around the sterilization chamber 219, and is disposed at a location closer to the sterilization chamber 219 than at least the below-described valve V3.

In the present exemplary embodiment, although the measuring pipe and the sterilization chamber are allowed to be communicated or prevented from being communicated with each other through the conduit by opening and closing the valve (V4) 213 and the valve (V3) 212, the measuring pipe and the sterilization chamber may be allowed to be communicated or prevented from being communicated with each other through the conduit by opening and closing any one of the valve (V4) 213 and the valve (V3) 212.

That is, the measuring pipe and the sterilization chamber may be allowed to be communicated or prevented from being communicated with each other through the conduit by opening and closing any one of the valve (V4) 213 and the valve (V3) 212.

The measuring pipe 214 is communicated through conduits with the concentration furnace 208, the vaporizing furnace 216, and the sterilization chamber 219.

The measuring pipe 214 is a unit for opening the valve (V1) 211 to introduce the sterilizer from the concentration furnace 208 and opening the valve (V3) 212 and the valve (V4) 213 to remove unnecessary air suctioned from the cartridge 205 and/or unnecessary air introduced into the concentration furnace 208 from the gas suctioning HEPA filter 210 and then introduced into the measuring pipe 214 from the concentration furnace 208 with the measuring pipe 214. Details of the measuring pipe 214 will be described below with reference to FIG. 10.

The valve (V2) 215 is a valve disposed in a conduit between the measuring pipe 214 and the vaporizing furnace 216, and is a valve configured so that the measuring pipe 214 and the vaporizing furnace 216 are communicated with each other through the conduit by opening the valve, and the measuring pipe 214 and the vaporizing furnace 216 are prevented from being communicated with each other through the conduit by closing the valve.

The vaporizing furnace 216 is communicated through conduits with the measuring pipe 214, the gas suctioning HEPA filter 210, and the sterilization chamber 219. The vaporizing furnace 216 is an application example of a vaporizing chamber of the present exemplary embodiment.

The pressure of the vaporizing furnace 216 is reduced by using the gas feeding vacuum pump 220 to vaporize the sterilizer.

The valve (V5) 217 is a valve disposed in a conduit between the vaporizing furnace 216 and the sterilization chamber 219, and is a valve configured so that the vaporizing furnace 216 and the sterilization chamber 219 are communicated with each other through the conduit by opening the valve, and the vaporizing furnace 216 and the sterilization chamber 219 are prevented from being communicated with each other through the conduit by closing the valve.

The valve (V9) 227 is a valve disposed in a conduit between the vaporizing furnace 216 and the gas suctioning HEPA filter 210, and is a valve configured so that the vaporizing furnace 216 and the gas suctioning HEPA filter 210 are communicated with each other through the conduit by opening the valve, and the vaporizing furnace 216 and the gas suctioning HEPA filter 210 are prevented from being communicated with each other through the conduit by closing the valve. That is, the valve (V9) 227 is a valve capable of opening/closing the communication of the vaporizing furnace 216 and the exterior gas (air).

The valve (V7) 226 is a valve disposed in a conduit between the sterilization chamber 219 and the gas suctioning HEPA filter 210, and is a valve configured so that the sterilization chamber 219 and the gas suctioning HEPA filter 210 are communicated with each other through the conduit by opening the valve, and the sterilization chamber 219 and the gas suctioning HEPA filter 210 are prevented from being communicated with each other through the conduit by closing the valve. That is, the valve (V7) 226 is a valve capable of opening/closing the communication of the sterilization chamber 219 and the exterior gas (air).

Although already described with reference to FIG. 1, the sterilization chamber (also referred to as a vacuum chamber) 219 is, for example, a casing having a predetermined capacity for sterilizing a sterilization target such as medical instruments and the like. A pressure in the sterilization chamber may be maintained at from the atmospheric pressure to a vacuum pressure. Further, a temperature in the sterilization chamber is maintained at a temperature within a predetermined range during a sterilization processing.

Further, a pressure sensor is disposed in the sterilization chamber 219, and a pressure (gas pressure) in the sterilization chamber 219 may be measured by the pressure sensor. The sterilization apparatus 100 determines whether a pressure (gas pressure) in the sterilization chamber 219 is a predetermined pressure by using the pressure in the sterilization chamber 219 measured by the pressure sensor.

The gas feeding vacuum pump 220 is a unit for suctioning the gas in the spaces in the sterilization chamber 219, in the vaporizing furnace 216, in the measuring pipe 214, in a conduit between the measuring pipe 214 and the vaporizing furnace 216, in a conduit between the vaporizing furnace 216 and the sterilization chamber 219, and in a conduit between the measuring pipe 214 and the sterilization chamber 219, and for reducing the pressures in the spaces to vacuum the spaces (a state in which the spaces are filled with a gas whose pressure is lower than the atmospheric pressure).

The gas feeding vacuum pump 220 is communicated with the sterilization chamber 219 through a conduit, and is communicated with the gas exhausting HEPA filter 221 through a conduit.

The gas exhausting HEPA filter 221 is communicated with the gas feeding vacuum pump 220 through a conduit. Further, the gas exhausting HEPA filter 221 is communicated with the gas exhausting/evaporating furnace 224 through a conduit. In addition, the gas exhausting HEPA filter 221 is communicated with the sterilizer decomposing unit 222 through a conduit. Furthermore, the gas exhausting HEPA filter 221 is communicated with the concentration furnace 208 through a conduit.

The gas exhausting HEPA filter 221 filters dust, fine dust, germs and the like in the gas sent through the conduit between the gas exhausting HEPA filter and the gas feeding vacuum pump 220 with an HEPA filter in the gas suctioned from the sterilization chamber 219 by the gas feeding vacuum pump 220 to clean the suctioned gas. Further, the cleaned gas is sent to the sterilizer decomposing unit 222 through a conduit between the sterilizer decomposing unit 222 and the gas exhausting HEPA filter 221, the molecules of the sterilizer contained in the gas are decomposed by the sterilizer decomposing unit 222, and the decomposed molecules are discharged outside the sterilization apparatus 100.

Further, the gas exhausting HEPA filter 221 cleans the gas exhausted from the concentration furnace 208 though a conduit between the concentration furnace 208 and the gas exhausting HEPA filter 221. The gas is water obtained by heating and vaporizing the sterilizer. However, The gas contains a finite amount of sterilizer in the concentration furnace 208, and thus is sent to the sterilizer decomposing unit 222 through a conduit between the sterilizer decomposing unit 222 and the gas exhausting HEPA filter 221. In addition, the molecules of the sterilizer contained in the gas are decomposed by the sterilizer decomposing unit 222, and the decomposed molecules are discharged outside the sterilization apparatus 100.

Further, the gas exhausting HEPA filter 221 cleans the evaporated sterilizer sent from the gas exhausting/evaporating furnace 224 through a conduit between the gas exhausting/evaporating furnace 224 and the gas exhausting HEPA filter 221. In addition, the cleaned sterilizer (gas) is sent to the sterilizer decomposing unit 222 through a conduit between the sterilizer decomposing unit 222 and the gas exhausting HEPA filter 221, the molecules of the sterilizer contained in the gas are decomposed by the sterilizer decomposing unit 222, and the decomposed molecules are discharged outside the sterilization apparatus 100.

The sterilizer decomposing unit 222 is communicated with the gas exhausting HEPA filter 221 through a conduit. The sterilizer decomposing unit 222 decomposes the molecules of the sterilizer contained in the gas sent from the conduit between the sterilizer decomposing unit 222 and the gas exhausting HEPA filter 221, and discharges the molecules produced through the decomposition outside the sterilization apparatus 100.

The gas exhausting HEPA filter 221 cleans the gas sent through the conduit, and thus fine dust or dust are not easily stored in the sterilizer decomposing unit 222, making it possible to extend a product life of the sterilizer decomposing unit 222.

The sterilizer decomposing unit 222 is a unit for decomposing the sterilizer, and is a unit capable of decomposing the evaporated hydrogen peroxide into water and oxygen by using manganese dioxide as a catalyst, for example, when the sterilizer is hydrogen peroxide or a hydrogen peroxide solution.

The liquid feeding rotary pump 223 is communicated with the gas exhausting/evaporating furnace 224 through a conduit and is communicated with the liquid sensor 204 through a conduit.

The liquid feeding rotary pump 223 is a unit for suctioning all the liquid sterilizer in the cartridge 205 by using a pump, and sending all the sterilizer sent through the conduit between the liquid sensor 204 and the liquid feeding rotary pump 223 to the gas exhausting/evaporating furnace 224 through the conduit between the liquid feeding rotary pump 223 and the gas exhausting/evaporating furnace 224.

The gas exhausting/evaporating furnace 224 is communicated with the liquid feeding rotary pump 223 through a conduit, and is communicated with the gas exhausting HEPA filter 221 through a conduit.

The gas exhausting/evaporating furnace 224 heats all the liquid sterilizer in the cartridge 205, which is sent through the conduit between the liquid feeding rotary pump 223 and the gas exhausting/evaporating furnace 224, by using a heater disposed in the gas exhausting/evaporating furnace 224, and evaporates all the sterilizer. Further, the evaporated sterilizer is sent to the gas exhausting HEPA filter 221 through the conduit between the gas exhausting HEPA filter 221 and the gas exhausting/evaporating furnace 224.

Figure 4B:
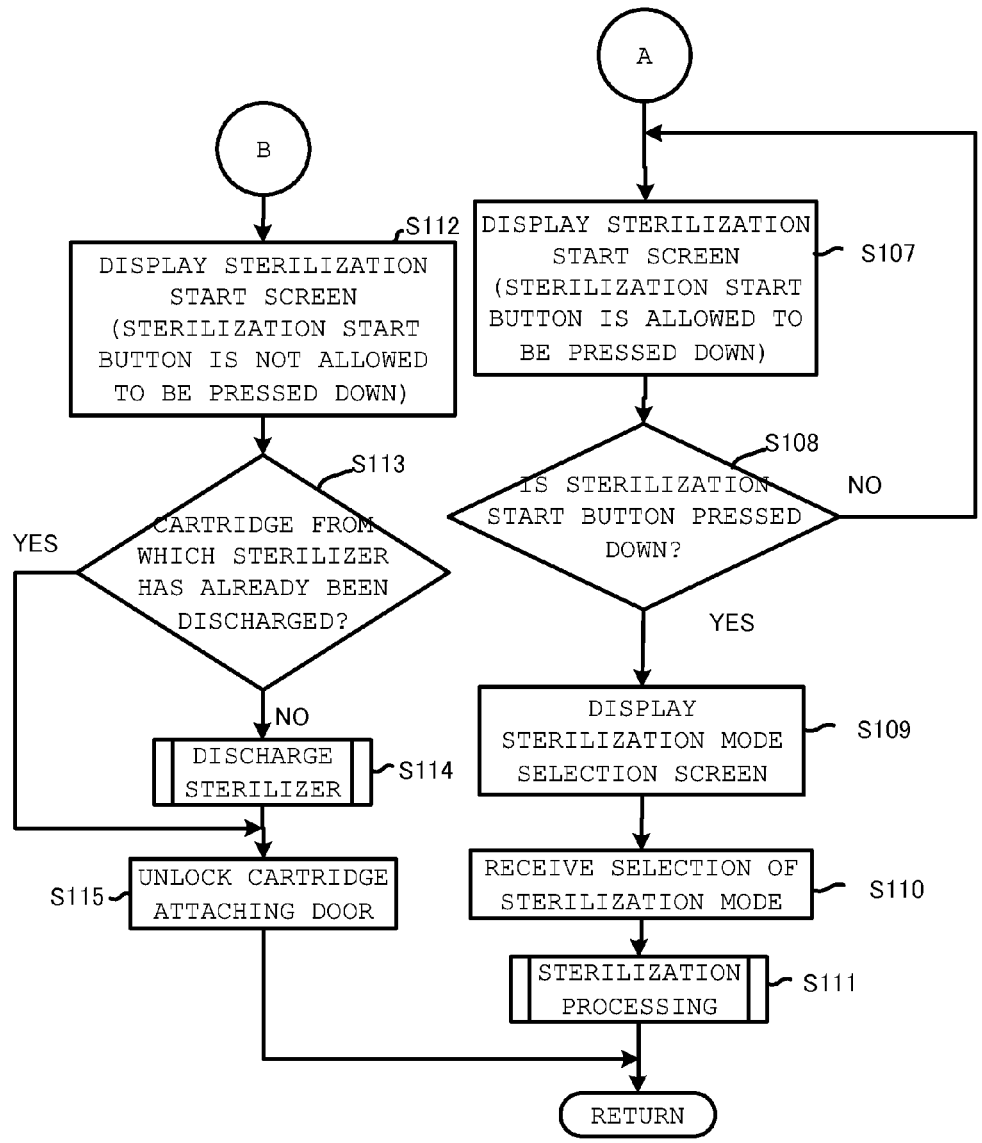
FIG. 4B is the second part of a flowchart illustrating an example of processes of a sterilization processing by the sterilization apparatus according to an exemplary embodiment

Next, an example of processes of the sterilization processing by the sterilization apparatus according to the present exemplary embodiment will be described with reference to the flowchart of FIGS. 4A and 4B. The processes (processing) illustrated in FIGS. 4A and 4B are performed by controlling the operations of the units in the sterilization apparatus with the operation processing unit 201 of the sterilization apparatus 100. That is, the processes (processing) illustrated in FIGS. 4A and 4B are performed by executing programs readable by the operation processing unit 201 of the sterilization apparatus 100 to control the operations of the units. FIGS. 4A and 4B include a flowchart illustrating an example of processes of a sterilization processing by the sterilization apparatus according to the present exemplary embodiment.

In the sterilization apparatus 100, when a power source is applied, first, the RF-ID reader/writer 206 (reading unit/writing unit) reads data from the RF-ID (storage medium) disposed below the cartridge 205 in operation S101.

In operation S101, the data read from the RF-ID (storage medium) includes a serial number as information for identifying the cartridge, a manufacturing date of the cartridge, a date and time (initial use date and time) when the cartridge is used in a sterilization apparatus for the first time, and a residual amount of the sterilizer filled in the cartridge. That is, a serial number, a manufacturing date, an initial user date and time, and a residual amount of a sterilizer are stored in the RF-ID (storage medium) disposed in the cartridge 205.

Further, the RF-ID of the cartridge used for the first time in the sterilization apparatus does not store an initial use date and time (a date and time when the cartridge is used for the first time in the sterilization apparatus). For this reason, the RF-ID of the cartridge used for the first time stores a serial number, a manufacturing date, and a residual amount of a sterilizer, but the RF-ID of the cartridge used after the second time stores a serial number, a manufacturing date, an initial use date and time, and a residual amount of a sterilizer.

Thus, in operation S101, a serial number, a manufacturing date, and a residual amount of a sterilizer are read from the RF-ID of the cartridge used for the first time. Further, a serial number, a manufacturing date, an initial use date and time, and a residual amount of a sterilizer are read from the RF-ID of the cartridge used after the second time.

For this reason, in operation S102, if a serial number, a manufacturing date, and a residual amount of a sterilizer may be read even though an initial use date and time is not read from the RF-ID of the cartridge used for the first time, it is determined that data may be read from the RF-ID.

Next, when it is determined that data may be read from the RF-ID in operation S101 (YES in operation S102), the sterilization apparatus 100 determines that the cartridge is disposed at an attachment position of the cartridge in the sterilization apparatus 100 and locks the cartridge attaching door 101 in operation S103. In this way, when data are read by the reading unit, the cartridge 205 is locked not to be extracted.

Further, for example, the syringe needle pricked in the cartridge is prevented from being withdrawn, so that the cartridge may not be extracted. That is, by pricking the syringe needle in the cartridge in operation S103, the sterilizer in the cartridge is allowed to be extracted and the cartridge may be prevented from being taken out.

In this way, when the cartridge is attached to an attachment position of the cartridge in the sterilization apparatus 100, the cartridge is locked not to be taken out.

When the cartridge in which the remaining sterilizer is stored is attached to the attachment position of the cartridge in the sterilization apparatus 100, the cartridge is locked so as not to be taken out, and thus the sterilizer may be prevented from contacting by the user.

As described above, when the cartridge is attached to the sterilization apparatus, the sterilization apparatus 100 locks the cartridge so that the cartridge may not be taken out. This is an application example of the lock unit of the present exemplary embodiment.

Further, the sterilization apparatus 100 determines whether a predetermined amount (for example, 8 millimeters) of sterilizer corresponding to a dose of sterilizer is present in the cartridge. More specifically, it is determined whether a residual amount of a sterilizer acquired from the RF-ID is larger than the predetermined amount corresponding to a dose. That is, when it is determined that the residual amount of a sterilizer is larger than the predetermined amount corresponding to a dose, it is determined that the predetermined amount of sterilizer corresponding to a dose is present in the cartridge (a sufficient sterilization processing may be performed) (YES in operation S104), and the processing proceeds to operation S105.

On the other hand, when it is determined that the residual amount of a sterilizer is smaller than the predetermined amount corresponding to a dose (for example, 8 millimeters), it is determined that the predetermined amount of sterilizer corresponding to a dose is not present in the cartridge (a sufficient sterilization processing may not be performed) (No in operation S104), and the processing proceeds to operation S112.

In operation S105, the sterilization apparatus 100 determines whether a predetermined period (for example, 13 months) has elapsed from a manufacturing date of the cartridge acquired from the RF-ID.

Further, when it is determined that a predetermined period has elapsed from the manufacturing date (YES in operation S105), it is determined that a sufficient sterilization processing may not be performed and the process proceeds to continuation connector B where the processing of operation S112 is performed (FIG. 4B). On the other hand, when it is determined that a predetermined period has not elapsed from the manufacturing date (NO in operation S105), it is determined that a sufficient sterilization processing may be performed and the processing proceeds to operation S106.

In operation S106, the sterilization apparatus 100 determines whether a predetermined period (for example, 2 weeks) has elapsed from an initial use date and time acquired from the RF-ID. For this reason, for example, it operation S101, the initial use date and time is not read from the RF-ID of the cartridge used for the first time, and thus in operation S106, it is determined that a predetermined period (for example, 2 weeks) has not elapsed from the initial use date and time acquired from the RF-ID (NO in operation S106).

Further, when it is determined that a predetermined period (for example, 2 weeks) has elapsed from the initial use date and time acquired from the RF-ID (YES in operation S106), it is determined that a sufficient sterilization processing may be performed and the processing of operation S112 is performed. On the other hand, when it is determined that a predetermined period (for example, 2 weeks) has not elapsed (NO in operation S106), it is determined that a sufficient sterilization processing may be performed and the processing proceeds to continuation connector A which continues in FIG. 4B.

FIG. 4B is the second part of a flowchart illustrating an example of processes of sterilizing processing by the sterilizing apparatus according to the exemplary embodiment.

From continuation connector A, in operation S107, the sterilization apparatus 100 displays a sterilization starting screen (screen 301 in FIG. 3) on the display unit 102. FIG. 3 is a diagram illustrating an example of a screen displayed on the display unit 102 of the sterilization apparatus 100. A "sterilization start button" is displayed on the sterilization starting screen 301. The "sterilization start button" 302 on the sterilization starting screen 301 displayed in operation S107 may be (actively) pressed down by the user.

Further, if the "sterilization start button" 302 is pressed down by the user (YES in operation S108), the sterilization apparatus 100 displays a sterilizing mode selecting screen 303 of FIG. 3 on the display unit 102. A button 304 for a "mode for concentrating a sterilizer to perform sterilization" and a button 305 for a "mode for performing sterilization without concentrating a sterilizer" are displayed on the sterilizing mode selecting screen 303.

The sterilization apparatus 100 receives a selection of any one of the button 304 for a "mode for concentrating a sterilizer to perform sterilization" and the button 305 for a "mode for performing sterilization without concentrating a sterilizer" from the user in operation S110, and performs a sterilization processing in operation S111 according to the mode of the button selected by the user. The details of the sterilization processing performed in operation S111 will be described below with reference to FIG. 5.

In this way, a mode for processing sterilization may be converted by one sterilization apparatus to be used according to an instruction of the user. That is, when the button 304 for a "mode for concentrating a sterilizer to perform sterilization" is pressed down by the user, the sterilizer is concentrated to perform the sterilization processing, and when the button 305 for a "mode for performing sterilization without concentrating a sterilizer" is pressed down, the sterilization processing is performed without concentrating the sterilizer. Further, if the sterilization processing in operation S111 is ended, the sterilization apparatus 100 returns the processing to operation S101.

From continuation connector B, in operation S112, the sterilization apparatus 100 displays a sterilization starting screen 301 in FIG. 3 on the display unit 102. However, the "sterilization start button" 302 on the sterilization starting screen 301 of FIG. 3 displayed in operation S112 is displayed not to be pressed down by the user (i.e., the "sterilization start button" 302 is not active). For this reason, it becomes possible for the user not to receive a sterilization processing starting instruction.

Further, the sterilization apparatus 100 determines in operation S113 whether the cartridge disposed at an attachment point of the cartridge is the cartridge which has already discharged the sterilizer, from the serial number acquired from the RF-ID in operation S101. More specifically, a serial number for identifying the cartridge from which the sterilizer has already discharged is stored in the memory (storage unit) in the sterilization apparatus 100, and by determining whether the serial number acquired from the RF-ID in operation S101 coincides with the serial number stored in the memory (storage unit), it is determined that the cartridge currently attached to the sterilization apparatus 100 is the cartridge from which the sterilizer has already been discharged.

Further, another example of determining whether the cartridge is a cartridge from which the sterilizer has been already discharged will also be described here. If the sterilizer is discharged in operation S114, the sterilization apparatus 100 stores information indicating that the cartridge is a cartridge from which the sterilizer has already been discharged in the RF-ID of the cartridge 205.

Further, in operation S113, the sterilization apparatus 100 determines whether the information indicating that the cartridge is a cartridge from which the sterilizer has already been discharged is read in operation S101, and when it is determined that the information may be read (YES in operation S113), the processing proceeds to operation S115, and when it is determined that the information may not be read (NO in operation S113), the processing proceeds to operation S114.

In this way, it is also possible to determine whether the cartridge currently attached to the sterilization apparatus 100 is a cartridge from which the sterilizer has already been discharged.

When it is determined that the cartridge attached to the sterilization apparatus 100 is a cartridge from which the sterilizer has already been discharged (YES in operation S113), the processing proceeds to operation S115. On the other hand, when it is determined that the cartridge is not a cartridge from which the sterilizer has already been discharged (NO in operation S113), a sterilizer discharging processing in operation S114 for suctioning all the residual amount of the liquid sterilizer left in the cartridge, decomposing all the sterilizer, and discharging the decomposed sterilizer outside the sterilization apparatus 100 is performed, and then the processing proceeds to operation S115. The details of the sterilizer discharging processing of operation S114 will be described below with reference to FIG. 9.

operation S114 is an application example of a discarding unit for discarding hydrogen peroxide solution in the cartridge. That is, the discarding unit decomposes all the hydrogen peroxide solution in the cartridge by using a catalyst to discard the hydrogen peroxide solution.

When it is determined that the data read in operation S101 satisfies predetermined conditions in operation S104, operation S105, and operation S106, the sterilizer in the cartridge 205 is discarded by the discarding unit.

That is, the predetermined conditions include a condition as to whether the amount of sterilizer used in a sterilization processing is left in the cartridge, a condition as to whether a predetermined time has elapsed from a manufacturing date of the cartridge, and a condition as to whether a predetermined time has elapsed from an initial use date and time of the cartridge.

If the processing of operation S114 is performed, the serial number read in operation S101 is stored in the memory (storage unit) in the sterilization apparatus 100 as a serial number for identifying the cartridge from which the sterilizer has already been discharged (discarded).

The sterilization apparatus 100 unlocks the cartridge attaching door 101 in operation S115. operation S115 is an application example of a releasing unit for releasing a lock by a lock unit.

In this way, before unlocking, a processing of suctioning out and discarding all the sterilizer in the cartridge 205 is performed in operation S114, and thus the sterilizer may be prevented from being touched by the user, while improving safety.

Figure 11:
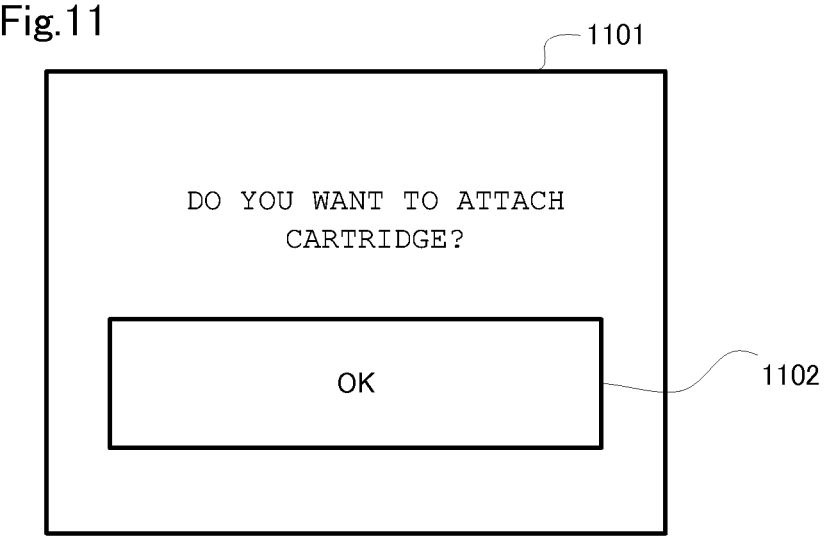
FIG. 11 is a diagram illustrating an example of a cartridge attachment requesting screen 1101 displayed on a display unit 102 of the sterilization apparatus 100.

When it is determined in operation S102 that data is not read from the RF-ID in operation S101 (NO in operation S102), the sterilization apparatus 100 determines that a cartridge is not disposed at an attachment position of the cartridge in the sterilization apparatus 100 and, in operation S116, displays a cartridge attachment requesting screen 1101 illustrated in FIG. 11.

FIG. 11 is a diagram illustrating an example of a cartridge attachment request screen 1101 displayed on a display unit 102 of the sterilization apparatus 100.

An "OK" button 1102 is displayed on the cartridge attachment request screen 1101.

Further, the sterilization apparatus 100 determines in operation S117 whether the "OK" button 1102 of the cartridge attachment requesting screen 1101 is pressed down by the user, and when the "OK" button 1102 is pressed down (YES in operation S117), the sterilization apparatus 100 unlocks the cartridge attaching door 101 in operation S118, and then returns the processing to operation S101. Meanwhile, when the "OK" button 1102 is not pressed down (NO in operation S117), the cartridge attachment request screen 1101 is continuously displayed.

The unlocking and locking of the cartridge attaching door 101 are performed by an operation by the lock operation control unit 202.

Figure 5:
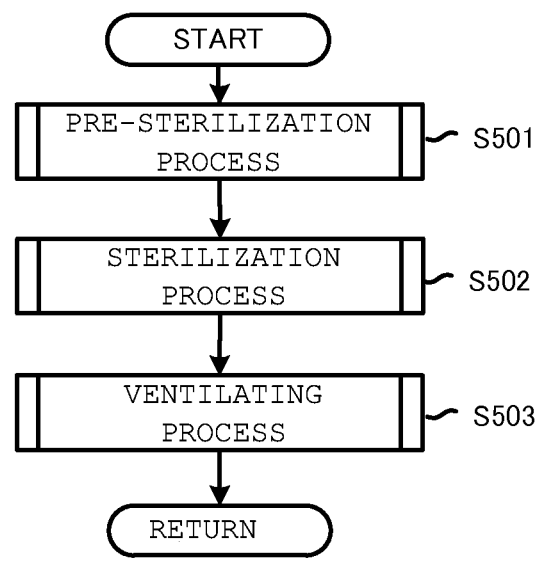
FIG. 5 is a flowchart illustrating an example of detailed processing of a sterilization processing illustrated in operation S111 of FIG. 4.

Next, an example of detailed sterilization processing illustrated in operation S111 of FIG. 4B will be described with reference to FIG. 5. FIG. 5 is a diagram illustrating an example of detailed sterilization processing illustrated in operation S111 of FIG. 4B. The processes (processing) illustrated in FIG. 5 are performed by controlling the operations of the units in the sterilization apparatus by the operation processing unit 201 of the sterilization apparatus 100. That is, the processes (processing) illustrated in FIG. 5 are performed by executing programs readable by the operation processing unit 201 of the sterilization apparatus 100 to control the operations of the units.

When the process illustrated in operation S501 of FIG. 5 starts, all the valves (the valve (V1) 211, the valve (V2) 215, the valve (V3) 212, the valve (V4) 213, the valve (V9) 227, and the valve (V7) 226) of the sterilization apparatus 100 remain closed.

First, in operation S501, the sterilization apparatus 100 performs a processing of a pre-sterilization process of operating the gas feeding vacuum pump 220, suctioning the gas in the sterilization chamber 219, and reducing the pressure in the sterilization chamber 219 to a predetermined pressure (for example, 45 Pa). The detailed processing of the processing of the pre-sterilization process will be described below with reference to FIG. 6.

Further, in operation S502, the sterilization apparatus 100 performs a sterilization process of introducing the sterilizer into the sterilization chamber 219 and sterilizing the sterilization target. The detailed processing of the sterilization process will be described below with reference to FIGS. 7A through 7D.

Next, in operation S503, the sterilization apparatus 100 performs a processing of a ventilating process for removing the sterilizer contained in the sterilization chamber 219 and the vaporizing furnace 216. The detailed processing of the ventilating process will be described below with reference to FIG. 8.

Figure 6:
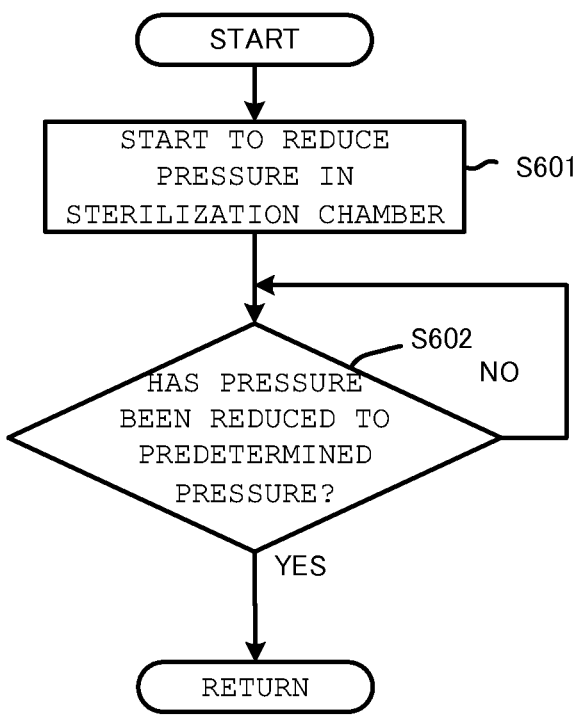
FIG. 6 is a flowchart illustrating an example of detailed processing of a pre-sterilization process illustrated in operation S501 of FIG. 5.

An example of detailed processing of a pre-sterilization process illustrated in operation S501 of FIG. 5 will be described with reference to FIG. 6. FIG. 6 is a flowchart illustrating an example of detailed processing of a pre-sterilization process illustrated in operation S501 of FIG. 5. The processes (processing) illustrated in FIG. 6 are performed by controlling the operations of the units in the sterilization apparatus by the operation processing unit 201 of the sterilization apparatus 100.

That is, the processes (processing) illustrated in FIG. 6 are performed by executing programs read by the operation processing unit 201 of the sterilization apparatus 100 to control the operations of the units.

First, in operation S601, the sterilization apparatus 100 starts processing of operating the gas feeding vacuum pump 220 and suctioning the gas in the sterilization chamber 219.

Further, in operation S602, the sterilization apparatus 100 determines whether the pressure (gas pressure) in the sterilization chamber 219 is reduced to a predetermined pressure (for example, 45 Pa). More specifically, it is determined whether the pressure in the sterilization chamber 219 measured by a pressure sensor disposed in the sterilization chamber 219 is reduced to a predetermined pressure (for example, 45 Pa).

When it is determined in operation S602 that the pressure (gas pressure) in the sterilization chamber 219 is not reduced to a predetermined pressure (for example, 45 Pa) (NO in operation S602), the sterilization apparatus 100 continuously operates the gas feeding vacuum pump 220, suctions the gas in the sterilization chamber 219, and reduces the pressure (gas pressure) in the sterilization chamber 219.

When it is determined in operation S602 that the pressure (gas pressure) in the sterilization chamber 219 is reduced to a predetermined pressure (for example, 45 Pa) (YES), the sterilization apparatus 100 continuously operates the gas feeding vacuum pump 220, suctions the gas in the sterilization chamber 219, and starts a processing of operation S502.

An example of detailed processing of a sterilization process illustrated in operation S502 of FIG. 5 will be described with reference to FIGS. 7A through 7D. FIGS. 7A through 7D include a flowchart illustrating an example of detailed processing of a sterilization process illustrated in operation S502 of FIG. 5. The processes (processing) illustrated in FIG. 7 A through 7D are performed by controlling the operations of the units in the sterilization apparatus by the operation processing unit 201 of the sterilization apparatus 100. That is, the processes (processing) illustrated in FIG. 7 A through 7D are performed by executing programs read by the operation processing unit 201 of the sterilization apparatus 100 to control the operations of the units.

Figure 7A:
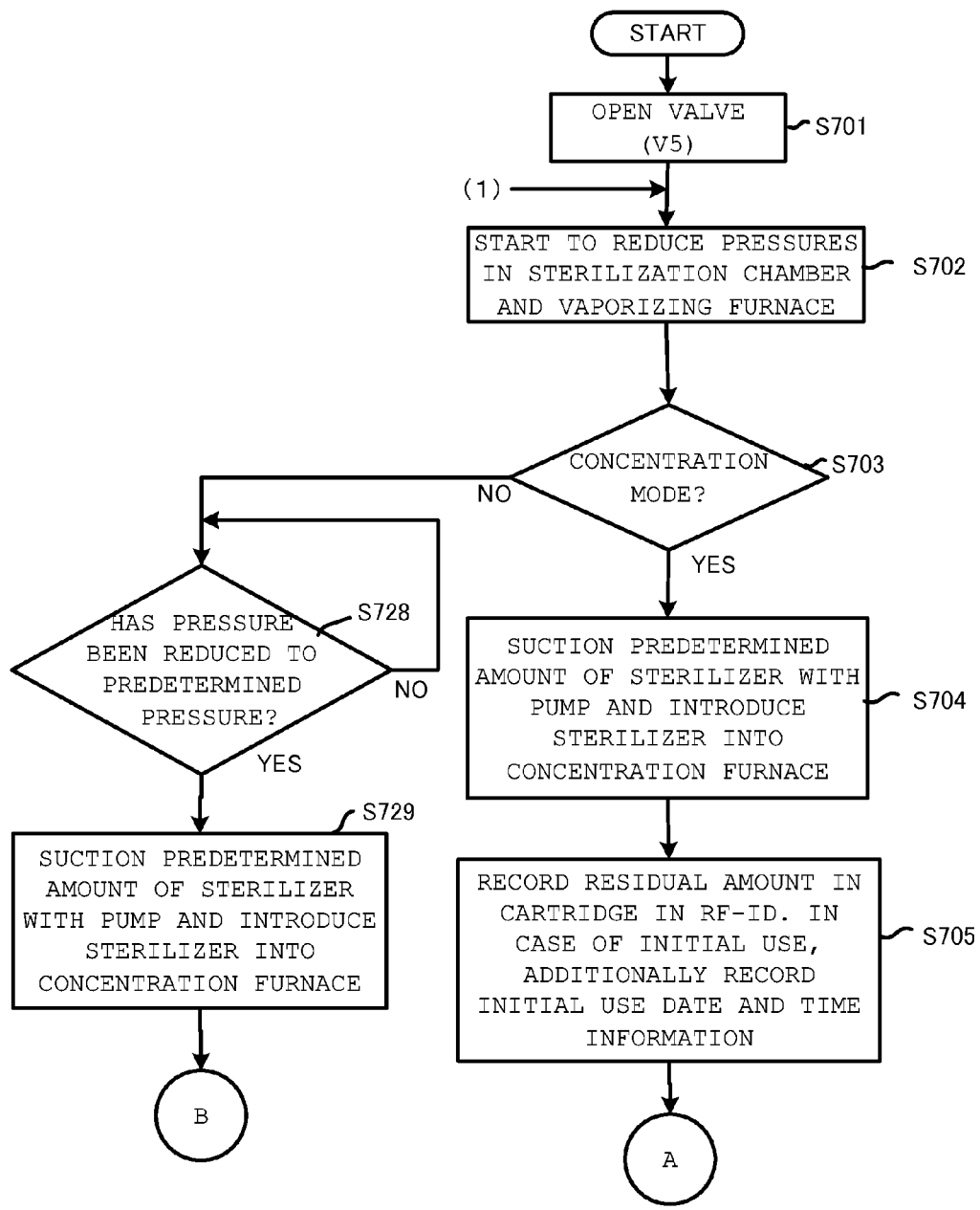
FIG. 7A is the first part of a flowchart illustrating an example of detailed processing of a sterilization process illustrated in operation S502 of FIG. 5.

FIG. 7A is the first part of a flowchart illustrating the example of detailed processing of a sterilizing process illustrated in S502 of FIG. 5.

First, in operation S701, the sterilization apparatus 100 opens the valve (V5) 217, and communicates a conduit between the sterilization chamber 219 and the vaporizing furnace 216. With this, currently, the gas in the sterilization chamber 219 is suctioned and pressure-reduced by the gas feeding vacuum pump 220, and thus the pressures in the sterilization chamber 219 and the vaporizing furnace 216 start to be reduced in operation S702.

Further, the sterilization apparatus 100 determines in operation S703 which one of the button 304 for the "mode for concentrating a sterilizer to perform sterilization" and the button 305 for the "mode for performing sterilization without concentrating a sterilizer" is pressed down in operation S110. When it is determined that the button 304 for the "mode for concentrating a sterilizer to perform sterilization" is pressed down (YES in operation S703), the processing proceeds to operation S704, and when it is determined that the button 305 for the "mode for performing sterilization without concentrating a sterilizer" is pressed down (NO in operation S703), the processing proceeds to operation S728.

First, a case where the button 304 for the "mode for concentrating a sterilizer to perform sterilization" is pressed down (the sterilizer is concentrated to perform sterilization) will be described.

In operation S704, the sterilization apparatus 100 operates the liquid feeding rotary pump 207 and suctions a predetermined amount (for example, 2 millimeters) of sterilizer in the cartridge 205. Further, the predetermined amount of suctioned sterilizer is introduced into the concentration furnace 208. The predetermined amount of sterilizer suctioned is the amount, for example, by which the space in the sterilization chamber 219 may be saturated with the sterilizer.

Further, in operation S705, the sterilization apparatus 100 records the residual amount of the sterilizer left in the cartridge 205 in the RF-ID of the cartridge 205 attached to the attachment position of the cartridge. More specifically, a value obtained by subtracting a predetermined amount (for example, 2 millimeters) of sterilizer suctioned from the cartridge 205 in operation S704 from the residual amount of a sterilizer in the cartridge 205 read in operation S101 is recorded in the RF-ID.

That is, a value obtained by subtracting a total sum of amounts of sterilizer suctioned from the cartridge 205 in operation S704 from the residual amount of a sterilizer in the cartridge 205 read in operation S101 is recorded in the RF-ID in operation S705.

Further, when an initial use date and time (date and time when the cartridge is used in the sterilization apparatus for the first time) read from the RF-ID in operation S101 does not contain information representing the date and time, the sterilization apparatus 100 determines at this time that the cartridge is used in the sterilization apparatus for the first time. That is, when an initial use date and time may not be read from the RF-ID in operation S101, the sterilization apparatus 100 determines at this time that the cartridge is used in the sterilization apparatus for the first time.

In this way, only when it is determined that the cartridge is used in the sterilization apparatus for the first time, current date and time information is also recorded in the RF-ID.

Figure 7B:
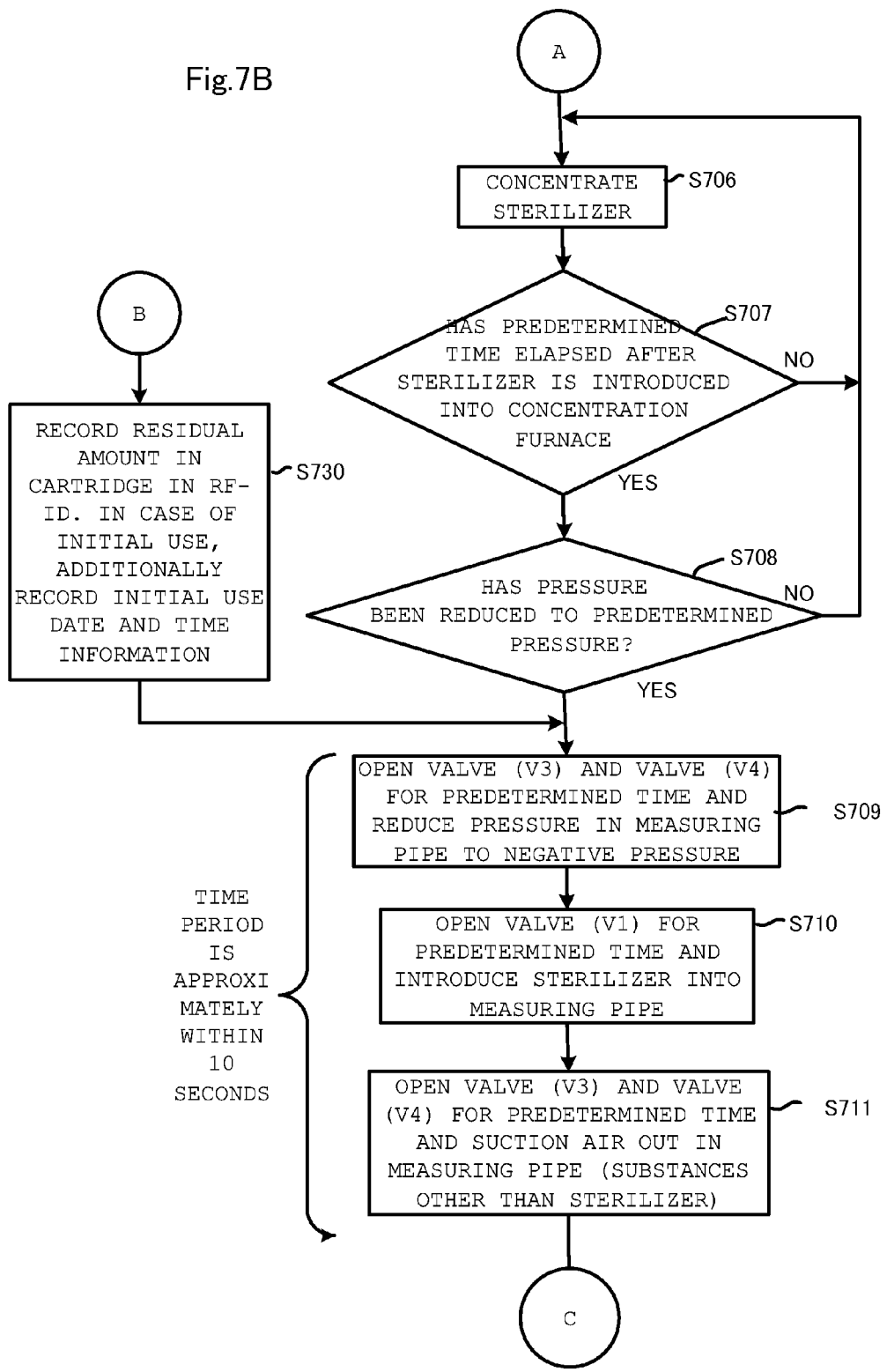
FIG. 7B is the second part of a flowchart illustrating an example of detailed processing of a sterilization process illustrated in operation S502 of FIG. 5.

Next, the sterilization apparatus 100 always heats a heater disposed in the concentration furnace 208 when a power source is applied to the sterilization apparatus 100, and thus the sterilizer introduced into the concentration furnace 208 in operation S704 is heated by the heat of the heater, and leading to continuation connector A which continues in FIG. 7B, and moisture contained in the sterilizer in the concentration furnace 208 is evaporated in operation S706.

FIG. 7B is the second part of a flowchart illustrating the example of detailed processing of a sterilizing process illustrated in S502 of FIG. 5.

From continuation connector A, the heater evaporates moisture contained in the sterilizer in the concentration furnace 208 in operation S706.

The reason why the heater disposed in the concentration furnace 208 is always heated when a power source is applied to the sterilization apparatus 100 is for immediately using the sterilization apparatus at any time, for example, in an operation room. In this way, the sterilization apparatus may be immediately used at any time by eliminating a time consumed to heat the heater of the concentration furnace.

That is, when the sterilizer is hydrogen peroxide (also referred to as hydrogen peroxide solution), the heater disposed in the concentration furnace 208 is heated to, for example, 80 degrees here. Accordingly, it becomes possible to mainly evaporate (vaporize) moisture and concentrate the sterilizer.

Next, in operation S707, the sterilization apparatus 100 determines whether a predetermined time (for example, 6 minutes) has elapsed after the sterilizer is introduced into the concentration furnace 208 in operation S704. Further, if it is determined that a predetermined time has elapsed after the sterilizer is introduced into the concentration furnace 208 (YES in operation S707), a processing proceeds to operation S708. On the other hand, when a predetermined time has not elapsed after the sterilizer is introduced into the concentration furnace 208 (NO in operation S707), the sterilizer is continuously concentrated while the sterilizer continuously remains introduced into the concentration furnace 208.

Next, in operation S708, the sterilization apparatus 100 determines whether the pressures in the sterilization chamber 219 and the vaporizing furnace 216 are reduced to a predetermined pressure (gas pressure) (for example, 500 Pa).

When the pressures in the sterilization chamber 219 and the vaporizing furnace 216 are reduced to a predetermined pressure (YES in operation S708), then in operation S709, the sterilization apparatus 100 opens the valve (V3) 212 and the valve (V4) 213 for a predetermined time (opens the valve (V3) 212 and the valve (V4) 213 for a predetermined time (for example, 3 seconds) and closes the valve (V3) 212 and the valve (V4) 213) to reduce the pressure in the measuring pipe 214. On the other hand, when the pressures in the sterilization chamber 219 and the vaporizing furnace 216 are not reduced to a predetermined pressure (NO in operation S708), the sterilizer is continuously concentrated. The process proceeds to continuation connector A.

Next, after the sterilization apparatus 100 opens the valve (V3) 212 and the valve (V4) 213 for a predetermined time, and closes the valve (V3) 212 and the valve (V4) 213 in operation S709, and opens the valve (V1) for a predetermined time (for example, 3 seconds) in operation S710, the pressure in the measuring pipe 214 is lower than the pressure of the concentration furnace 208 (exterior), and thus the sterilizer introduced into the concentration furnace 208 is suctioned into the measuring pipe 214 in operation S710. Here, by opening the valve (V1) for a predetermined time and closing the valve (V1), the sterilizer introduced into the concentration furnace 208 is suctioned into the measuring pipe 214. The air in the concentration furnace 208 as well as the sterilizer is also suctioned into the measuring pipe 214.

Also thereafter, the pressure in the sterilization chamber 219 is continuously reduced by the gas feeding vacuum pump 220. For this reason, the pressure in the sterilization chamber 219 becomes lower than the pressure in the measuring pipe. More specifically, the pressure in the sterilization chamber 219 is approximately 400 Pa, and the pressure in the measuring pipe is a value corresponding to approximately the atmospheric pressure (101325 Pa). The reason why the pressure in the measuring pipe is increased up to the vicinity of the atmospheric pressure is that the air in the concentration furnace 208 as well as the sterilizer is also suctioned into the measuring pipe 214.

Next, in operation S711, the sterilization apparatus 100 opens the valve (V3) 212 and the valve (V4) 213 for a predetermined time (for example, 3 seconds), and suctions out the air in the measuring pipe (not containing the liquid sterilizer) to the sterilization chamber 219. That is, here, if the valve (V3) 212 and the valve (V4) 213 are opened and the predetermined time elapses, the valve (V3) 212 and the valve (V4) 213 are closed. The process proceeds to continuation connector C which continues in FIG. 7C.

Figure 7C:
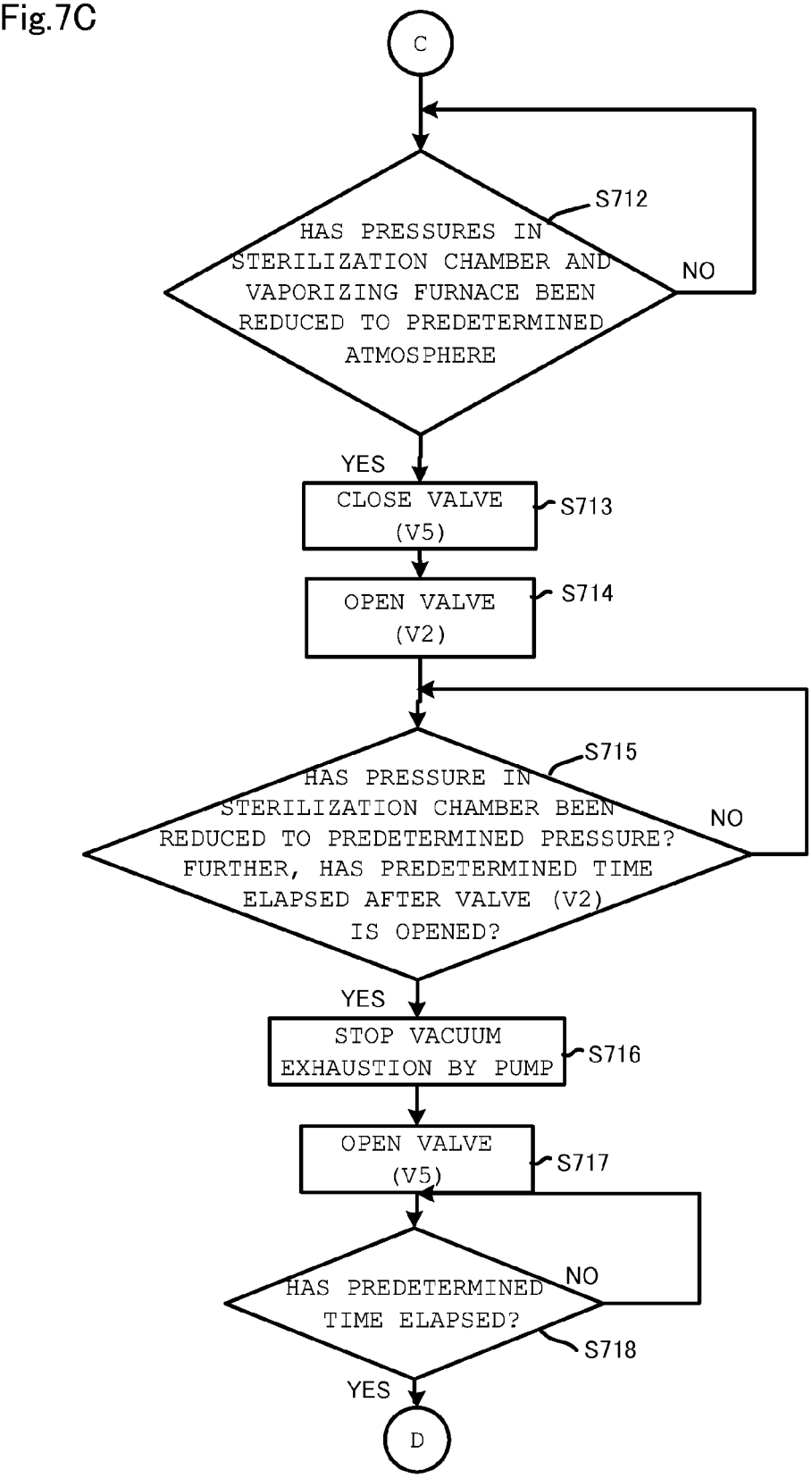
FIG. 7C is the third part of a flowchart illustrating an example of detailed processing of a sterilization process illustrated in operation S502 of FIG. 5.

FIG. 7C is the third part of a flowchart illustrating the example of detailed processing of a sterilizing process illustrated in S502 of FIG. 5.

Next, the sterilization apparatus 100 determines whether the pressures in the sterilization chamber 219 and the vaporizing furnace 216 are reduced to a predetermined pressure (for example, 80 Pa), and when it is determined that the pressures are reduced in operation S712 (YES in operation S712), the valve (V5) 217 is closed in operation S713.

Further, the sterilization apparatus 100 opens the valve (V2) 215 in operation S714. Accordingly, the sterilizer in the measuring pipe 214 is suctioned into the vaporizing furnace 216 and is vaporized in the vaporizing furnace 216. The sterilizer is vaporized in the vaporizing furnace as molecular clusters.

The interior of the sterilization chamber has a capacity larger than that of the vaporizing furnace, and the sterilizer is vaporized as molecular clusters in the vaporizing furnace. It is because the capacity of the vaporizing furnace is smaller than that of the sterilization chamber, and thus the molecular clusters may be easily formed by the molecular force as the distances between the molecules of the sterilizer in the sterilization chamber become close.

In this case also, the gas feeding vacuum pump 220 continuously suctions the gas in the sterilization chamber 219 and reduces the pressure in the sterilization chamber 219. The pressure in the vaporizing furnace 216 into which the sterilizer in the measuring pipe 214 is suctioned increases. That is, the pressure in the vaporizing furnace 216 becomes higher than the pressure in the sterilization chamber 219.

Next, the sterilization apparatus 100 determines in operation S715 whether the pressure in the sterilization chamber 219 is reduced to a predetermined pressure (for example, 50 Pa) and a predetermined time has elapsed after the valve (V2) 215 is opened in operation S714, and when the pressure in the sterilization chamber 219 is reduced to a predetermined pressure (for example, 50 Pa) and a predetermined time has elapsed after the valve (V2) 215 is opened in operation S714 (YES in operation S715), a suctioning (vacuuming) operation on the sterilization chamber 219 by the gas feeding vacuum pump 220 is stopped in operation S716, and the valve (V5) 217 is opened in operation S717. Accordingly, the sterilizer vaporized in the sterilization chamber 219 may be diffused to sterilize the sterilization target.

The sterilizer is diffused because the pressure (for example, 50 Pa) in the sterilization chamber 219 is lower than the pressure in the vaporizing furnace 216. The molecular clusters of the diffused sterilizer in the vaporizing furnace are further classified, and thus the sterilizer may be further diffused in the sterilization chamber to improve the sterilizing operation. Further, a small cavity of the sterilization target may be effectively sterilized.

Figure 7D:
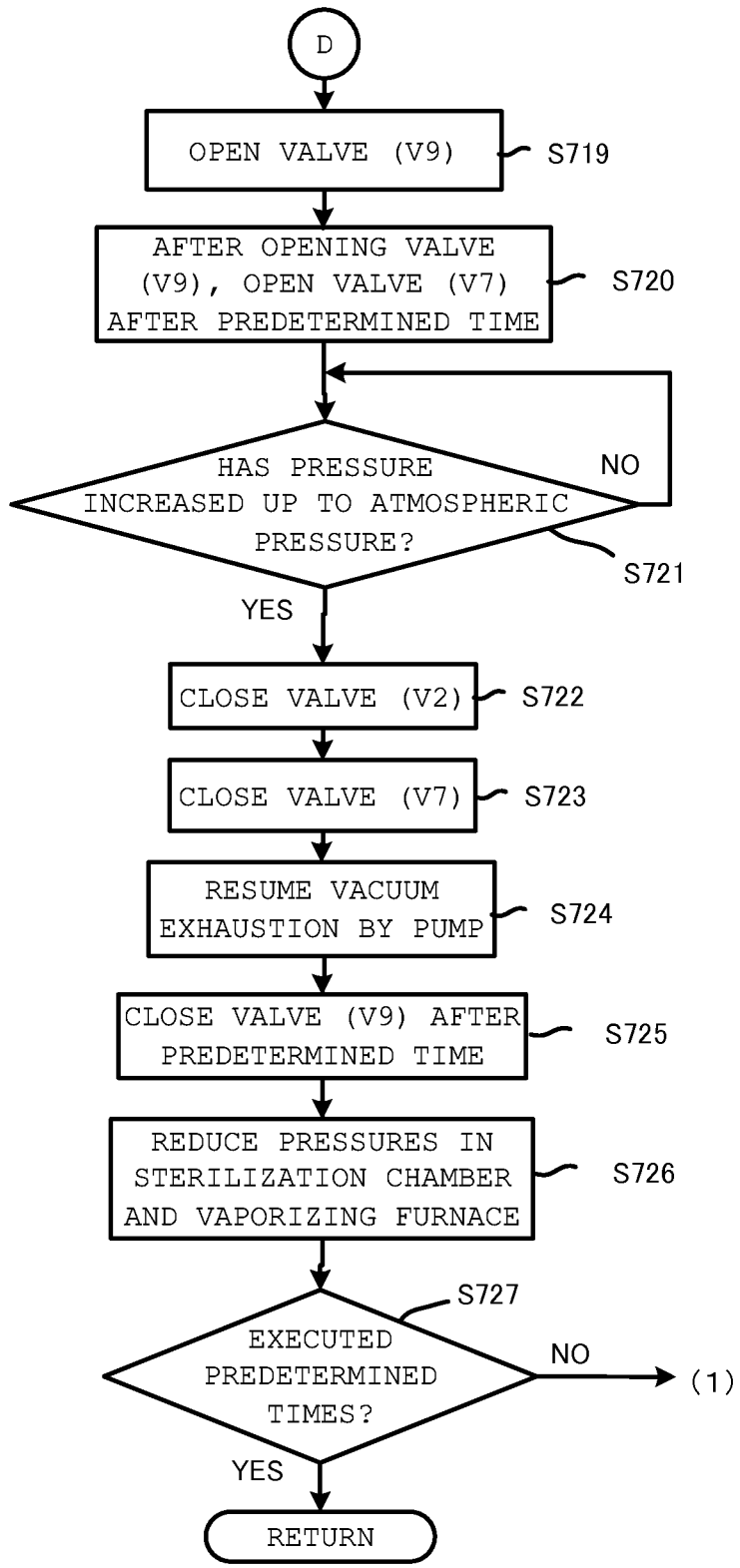
FIG. 7D is the fourth part of a flowchart illustrating an example of detailed processing of a sterilization process illustrated in operation S502 of FIG. 5.

Further, it is determined in operation S717 whether a predetermined time (for example, 330 seconds) has elapsed after the valve (V5) 217 is opened, and if it is determined that a predetermined time (for example, 330 seconds) has elapsed after the valve (V5) 217 is opened (YES in operation S718), the valve (V9) 227 is opened in operation S719 as shown in FIG. 7D.

Accordingly, the pressures in the vaporizing furnace 216 and the sterilization chamber 219 are lower than the pressure outside the sterilization apparatus 100, and thus the exterior gas (air) outside the sterilization apparatus 100 cleaned in the gas suctioning HEPA filter is suctioned into the vaporizing furnace 216. Further, the sterilizer filled in the vaporizing furnace 216 as a gas and the sterilizer adhered to a surface of the interior of the vaporizing furnace 216 are carried into the sterilization chamber 219 by the air carried into the vaporizing furnace 216, and a sterilizing operation on the sterilization target present in the sterilization chamber 219 is improved. Accordingly, for example, a sterilizing operation on portions, such as a deep portion of a thin tube of the sterilization target, which may not be easily sterilized, is improved. The process proceeds to continuation connector D which continues in FIG. 7D.

FIG. 7D is the fourth part of a flowchart illustrating the example of detailed processing of a sterilizing process illustrated in S502 of FIG. 5.

Further from continuation connector D, in operation S719, if a predetermined time (15 seconds) has elapsed after the valve (V9) 227 is opened, the sterilization apparatus 100 opens the valve (V7) 226, and the exterior gas (air) outside the sterilization apparatus 100 cleaned by the gas suctioning HEPA filter 210 is suctioned into the sterilization chamber 219. This is because the pressures in the sterilization chamber 219 and the vaporizing furnace 216 are lower than the pressure outside the sterilization apparatus 100, and thus the exterior gas (air) outside the sterilization apparatus 100 is suctioned into the sterilization chamber 219.

Accordingly, a sterilizing operation on portions (in particular, a cavity portion), such as a deep portion of a thin tube of the sterilization target, which may not be easily sterilized, is improved.

Next, the sterilization apparatus 100 determines whether the pressures in the sterilization chamber 219 and the vaporizing furnace 216 increase up to the atmospheric pressure, and when it is determined that the atmospheres increase up to the atmospheric pressure (YES in operation S721), the valve (V2) 215 is closed in operation S722.

Next, the sterilization apparatus 100 closes the valve (V7) 226 in operation S723, and resumes a suctioning (vacuuming) operation on the interior of the sterilization chamber 219 by the gas feeding vacuum pump 220 in operation S724. Accordingly, the exterior gas (air) outside the sterilization apparatus 100 cleaned by the gas suctioning HEPA filter 210 is suctioned into the vaporizing furnace 216 through a conduit with which the gas suctioning HEPA filter 210 and the vaporizing furnace 216 are communicated. Further, the sterilizer filled in the vaporizing furnace 216 as a gas and the sterilizer adhered to a surface of the interior of the vaporizing furnace 216 are carried into the sterilization chamber 219 by the air carried into the vaporizing furnace 216.

Accordingly, a sterilizing operation on portions (in particular, a cavity portion), such as a deep portion of a thin tube of the sterilization target, which may not be easily sterilized, is improved, and the sterilizer in the vaporizing furnace 216 may be effectively reduced.

Further, after resuming a suctioning (vacuuming) operation on the interior of the sterilization chamber 219 by the gas feeding vacuum pump 220 in operation S724, then in operation S725, the sterilization apparatus 100 closes the valve (V9) 227 after a predetermined time (for example, 15 seconds).

In this case also, a suctioning (vacuuming) operation on the interior of the sterilization chamber 219 by the gas feeding vacuum pump 220 is continuously performed, and the interiors of the sterilization chamber 219 and the vaporizing furnace 216 are airtight through operation S725, and the pressures in the sterilization chamber 219 and the vaporizing furnace 216 are reduced in operation S726.

Next, the sterilization apparatus 100 determines in operation S727 whether processing of steps S702 to S726 are performed a predetermined number of times (for example, four times), and when it is determined that the steps are performed (YES in operation S727), the processing proceeds to operation S503.

On the other hand, when it is determined that the processing of steps S702 to S726 are not performed a predetermined number of times (NO in operation S727), the processing from operation S702 are performed again. In this way, as the processing of steps S702 to S726 are performed the predetermined number of times, the effect of the sterilizing operation on the sterilization target increases, and the sterilization target may be sufficiently sterilized.

Next, a case where it is determined in operation S703 that the button 305 for the "mode for performing sterilization without concentrating a sterilizer" is pressed down (a sterilization is performed without concentrating the sterilizer) will be described.

When it is determined in operation S703 that the button 305 for the "mode for performing sterilization without concentrating a sterilizer" is pressed down (NO in operation S703), then in operation S728, it is determined whether the pressures in the sterilization chamber 219 and the vaporizing furnace 216 are reduced to a predetermined pressure (for example, 1000 Pa).

Further, when it is determined that the pressures in the sterilization chamber 219 and the vaporizing furnace 216 are reduced to a predetermined pressure (for example, 100 Pa) (YES in operation S728), the sterilization apparatus 100 operates the liquid feeding rotary pump 207, and suctions the sterilizer in the cartridge 205 by a predetermined amount (for example, 2 millimeters). In addition, the predetermined amount of suctioned sterilizer is introduced into the concentration furnace 208 in operation S729.

The predetermined amount of sterilizer suctioned here is, for example, an amount by which the space in the sterilization chamber 219 may be saturated with the sterilizer.

The process proceeds to continuation connector B which continues in FIG. 7B.

Refer to FIG. 7B, from continuation connector B shown in FIG. 7A, in operation S730, the sterilization apparatus 100 records the residual amount of sterilizer left in the cartridge 205 in the RF-ID of the cartridge 205 attached to the attachment point of the cartridge. More specifically, a value obtained by subtracting a predetermined amount (for example, 2 millimeters) of sterilizer suctioned from the cartridge 205 in operation S729 from the residual amount of sterilizer in the cartridge 205 read in operation S101 is stored in the RF-ID.

In a case where a predetermined amount of sterilizer suctioned from the cartridge 205, which corresponds to a dose, is, for example, 2 millimeters and in a case where it is determined it is not performed the predetermined number of times (NO in operation S727), and the processing from operation S702 is performed, for example, for the second time, since a total sum of an amount of the sterilizer suctioned from the cartridge 205 in operation S729 is 4 millimeters (2 millimeters (the predetermined amount)×twice), a value obtained by subtracting a total sum of the sterilizer suctioned from the cartridge 205 in operation S729, which is 4 millimeters from the residual amount of the sterilizer in the cartridge 205 read in operation S101, is stored in the RF-ID in operation S730.

That is, a value obtained by subtracting a total sum of predetermined amounts of sterilizer suctioned from the cartridge 205 in operation S729 from the residual amount of sterilizer in the cartridge 205 read in operation S101 is stored in the RF-ID in operation S730.

Further, in operation S730, when an initial use date and time (date and time when the cartridge is used in the sterilization apparatus for the first time) read from the RF-ID in operation S101 does not contain information representing the date and time, the sterilization apparatus 100 determines at this time that the cartridge is used in the sterilization apparatus for the first time. That is, when an initial use date and time may not be read from the RF-ID in operation S101, the sterilization apparatus 100 determines at this time that the cartridge is used in the sterilization apparatus for the first time.

In this way, only when it is determined that the cartridge is used in the sterilization apparatus for the first time, current date and time information is also recorded in the RF-ID. Further, if the processing of operation S730 is performed, the sterilization apparatus 100 performs the processing from the above-described operation S709.

If the pressure in the sterilization chamber 219 becomes a predetermined pressure (for example, 1000 Pa) in operation S728, the sterilizer starts to be suctioned in operation S729 and the pressure is below 500 Pa when all the sterilizer is suctioned in operation S729, and thus the processing may efficiently proceed to operation S709.

In this way, after the pressures in the sterilization chamber 219 and the vaporizing furnace 216 are reduced to a predetermined pressure (for example, 1000 Pa) at which a pressure in the measuring pipe 214 starts to be reduced, a predetermined amount of suctioned sterilizer may be introduced into the concentration furnace 208, a pressure in the measuring pipe 214 may be reduced immediately in operation S709, and then the sterilizer in the concentration furnace 208 is introduced into the measuring pipe in operation S710, and thus the sterilizer may be immediately introduced from the concentration furnace 208 into the measuring pipe 214. That is, the sterilizer may be introduced into the measuring pipe 214 without being concentrated in the concentration furnace 208.

Figure 8A:
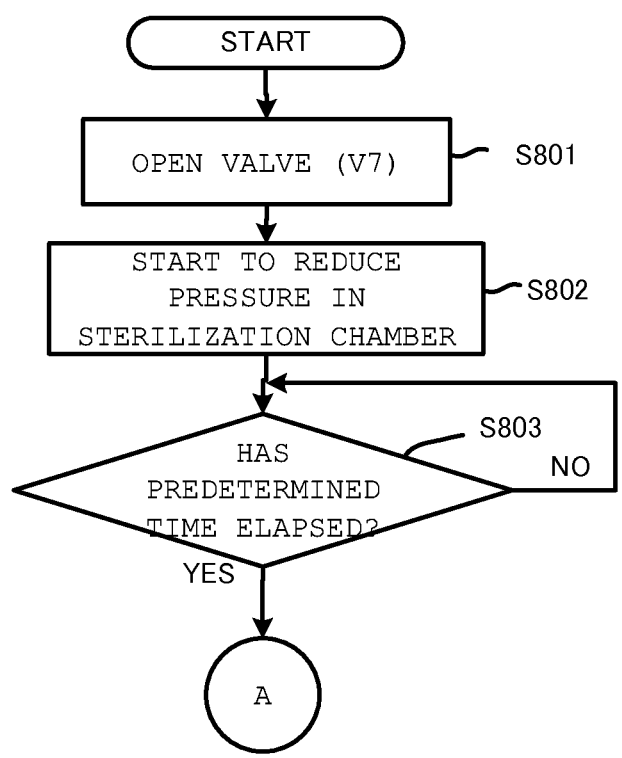
FIG. 8A is the first part of a flowchart illustrating an example of detailed processing of a ventilating process illustrated in operation S503 of FIG. 5.

An example of detailed processing of a ventilating process illustrated in operation S503 of FIG. 5 will be described with reference to FIGS. 8A and 8B. FIG. 8A is the first part of a flowchart illustrating an example of detailed processing of a ventilating process illustrated in S503 of FIG. 5.

Figure 8B:
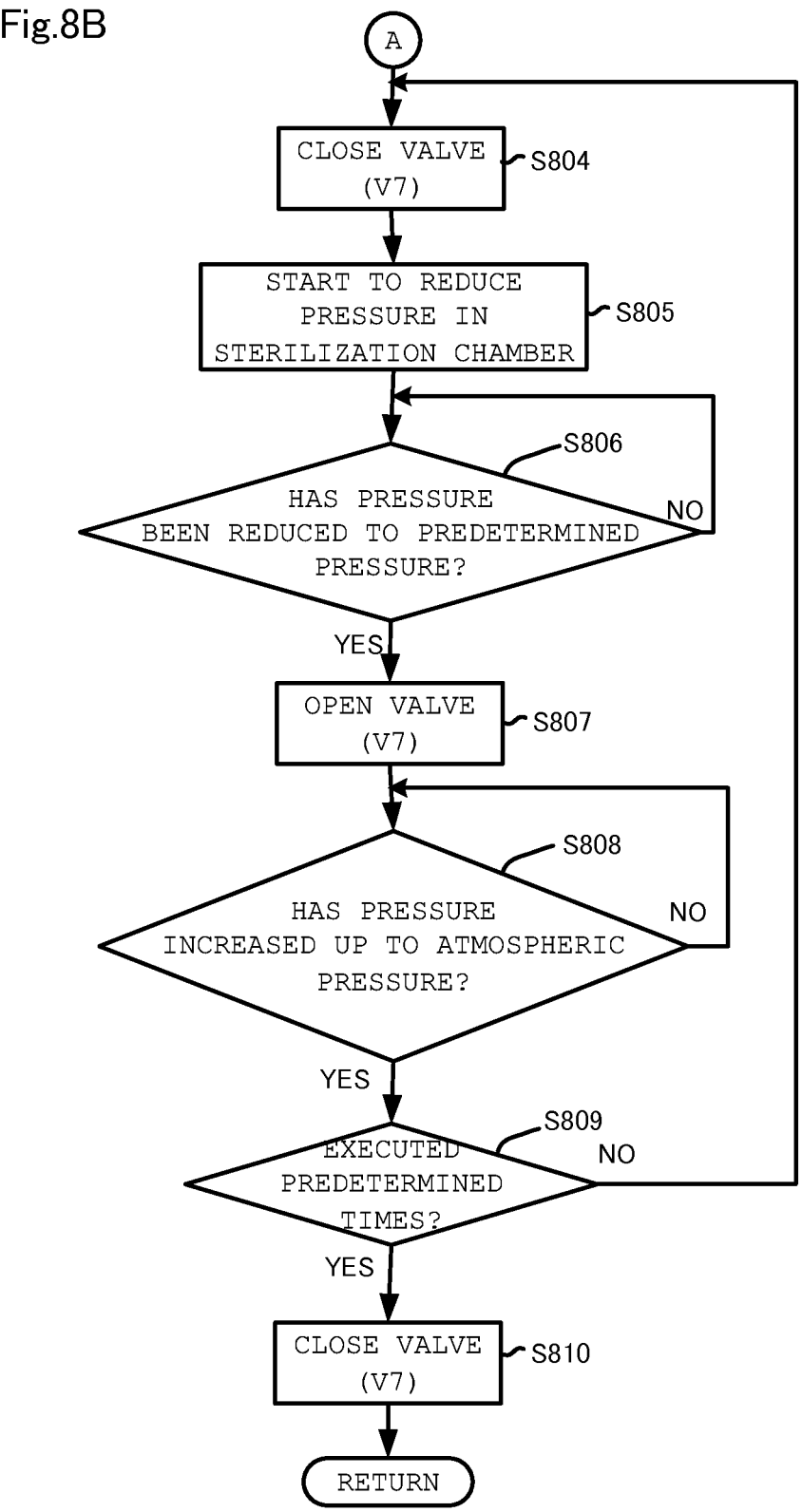
FIG. 8B is the second part of a flowchart illustrating an example of detailed processing of a ventilating process illustrated in operation S503 of FIG. 5.

The processes (processing) illustrated in FIGS. 8A and 8B are performed by controlling the operations of the units in the sterilization apparatus by the operation processing unit 201 of the sterilization apparatus 100. That is, the processes (processing) illustrated in FIG. 8 are performed by executing programs read by the operation processing unit 201 of the sterilization apparatus 100 to control the operations of the units.

First, the sterilization apparatus 100 opens the valve (V7) 226 in operation S801. Further, the sterilization apparatus 100 continuously performs a suctioning (vacuuming) operation on the interior of the sterilization chamber 219 by the gas feeding vacuum pump 220 in operation S802.

If the valve (V7) 226 is opened in operation S801 and a suctioning (vacuuming) operation is performed on the interior of the sterilization chamber 219 by the gas feeding vacuum pump 220 in operation S802, and then a predetermined time has elapsed (YES in operation S803), the process proceeds to continuation connector A which continues in FIG. 8B.

FIG. 8B is the second part of a flowchart illustrating the example of detailed processing of a ventilating process illustrated in S503 of FIG. 5.

From continuation connector A, the valve (V7) 226 is closed in operation S804, and a suctioning (vacuuming) operation on the interior of the sterilization chamber 219 by the gas feeding vacuum pump 220 is continuously performed. Accordingly, the pressure in the sterilization chamber 219 is reduced.

Next, if the pressure in the sterilization chamber 219 is reduced to a predetermined pressure (50 Pa) (YES in operation S806), the sterilization apparatus 100 opens the valve (V7) 226 in operation S807. Accordingly, the exterior gas (air) outside the sterilization apparatus 100 cleaned by the gas suctioning HEPA filter 210 is suctioned into the sterilization chamber 219. This is because the pressure in the sterilization chamber 219 is lower than the pressure outside the sterilization apparatus 100, and thus the exterior gas (air) outside the sterilization apparatus 100 is suctioned into the sterilization chamber 219.

Then, it is determined whether the atmosphere in the sterilization chamber 219 increases up to the atmospheric pressure. When it is determined that the pressure in the sterilization chamber 219 has increased up to the atmospheric pressure (YES in operation S808), then in operation S809, the sterilization apparatus 100 determines whether the processing of steps S804 to S808 is performed a predetermined number of times (for example, four times), and when the processing of steps S804 to S808 are performed the predetermined number of times (for example, four times) (YES in operation S809), the sterilization apparatus 100 closes the valve (V7) 226 in operation S810 and ends the ventilating process.

On the other hand, when the processing of steps S804 to S808 are not performed a predetermined number of times (for example, four times) (NO in operation S809), the processing starts from operation S804 again.

Accordingly, the sterilizer adhered to a surface of the interior of the sterilization chamber 219 and the sterilizer left in the sterilization chamber 219 as a gas are suctioned by the gas feeding vacuum pump 220. The suctioned gas (containing the sterilizer) passes through the gas exhausting HEPA filter 221, the sterilizer is decomposed by the sterilizer decomposing unit 222, and the decomposed molecules are discharged to the outside.

Figure 9:
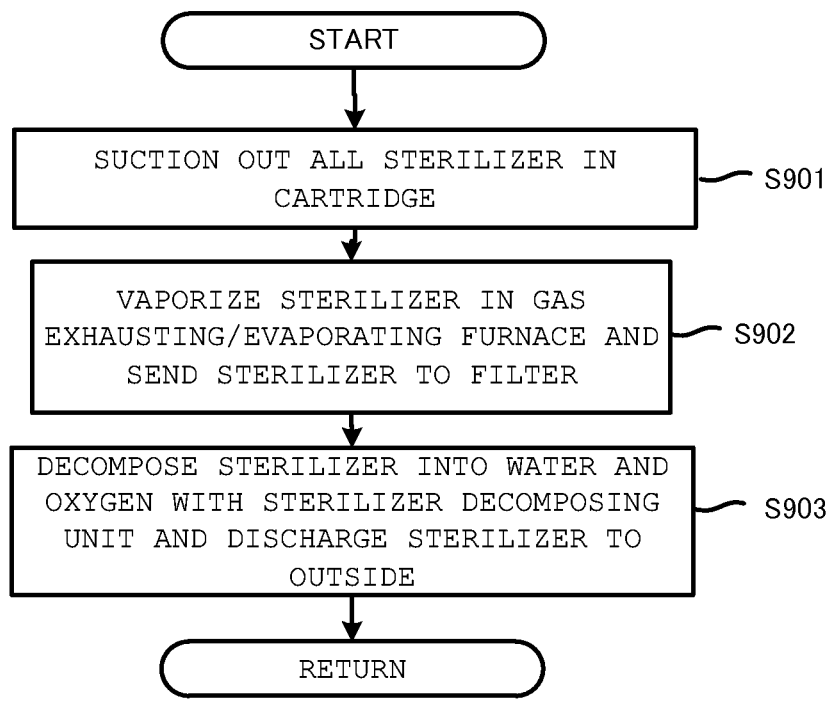
FIG. 9 is a flowchart illustrating an example of detailed processing of a sterilization/discharging processing illustrated in operation S114 of FIG. 4B.

Next, an example of detailed processing of the sterilizer discharging processing illustrated in S114 of FIG. 4 will be described with reference to FIG. 9. FIG. 9 is a view illustrating an example of detailed processing of the sterilizer discharging processing illustrated in S114 of FIG. 4. The processes (processing) illustrated in FIG. 9 are performed by controlling the operations of the units in the sterilization apparatus with the operation processing unit 201 of the sterilization apparatus 100. That is, the processes (processing) illustrated in FIG. 9 are performed by executing programs read by the operation processing unit 201 of the sterilization apparatus 100 to control the operations of the units.

First, in the sterilization apparatus 100, the liquid feeding rotary pump 223 suctions all the liquid sterilizer in the cartridge 205, and sends all the sterilizer sent through the conduit between the liquid sensor 204 and the liquid feeding rotary pump 223 to the gas exhausting/evaporating furnace 224 through the conduit between the liquid feeding rotary pump 223 and the gas exhausting/evaporating furnace 224 in operation S901.

Further, in the sterilization apparatus 100, the gas exhausting/evaporating furnace 224 heats all the liquid sterilizer stored in the gas exhausting/evaporating furnace 224 sent through the conduit between the liquid feeding rotary pump 223 and the gas exhausting/evaporating furnace 224 with a heater disposed in the gas exhausting/evaporating furnace 224, and evaporates all the sterilizer. In addition, the evaporated sterilizer is sent to the gas exhausting HEPA filter 221 through the conduit between the gas exhausting HEPA filter 221 and the gas exhausting/evaporating furnace 224 in operation S902.

The heater disposed in the gas exhausting/evaporating furnace 224 is heated to a temperature higher than, for example, a boiling point (a boiling point of hydrogen peroxide is 141 degrees) of the sterilizer (hydrogen peroxide). For this reason, all the sterilizer is vaporized by the gas exhausting/evaporating furnace 224.

Further, the sterilization apparatus 100 cleans the vaporized sterilizer sent through a conduit between the gas exhausting/evaporating furnace 224 and the gas exhausting HEPA filter 221 with the gas exhausting HEPA filter 221, and the cleaned gas (containing the sterilizer) is sent to the sterilizer decomposing unit 222 through a conduit between the sterilizer decomposing unit 222 and the gas exhausting HEPA filter 221.

Further, the sterilizer decomposing unit 222 decomposes the molecules of the sterilizer contained in the gas sent from the conduit between the sterilizer decomposing unit 222 and the gas exhausting HEPA filter 221, and discharges the molecules produced through the decomposition outside the sterilization apparatus 100 in operation S903.

A block configuration of a hardware configuration of a concentration furnace 208, a valve (V1) 211, a valve (V3) 212, a valve (V4) 213, a measuring pipe 214, a valve (V2) 215, a vaporizing furnace 216, a valve (V5) 217, and a valve (V9) 227 of the sterilization apparatus 100 according to the present exemplary embodiment will be described with reference to FIG. 10.

Figure 10:
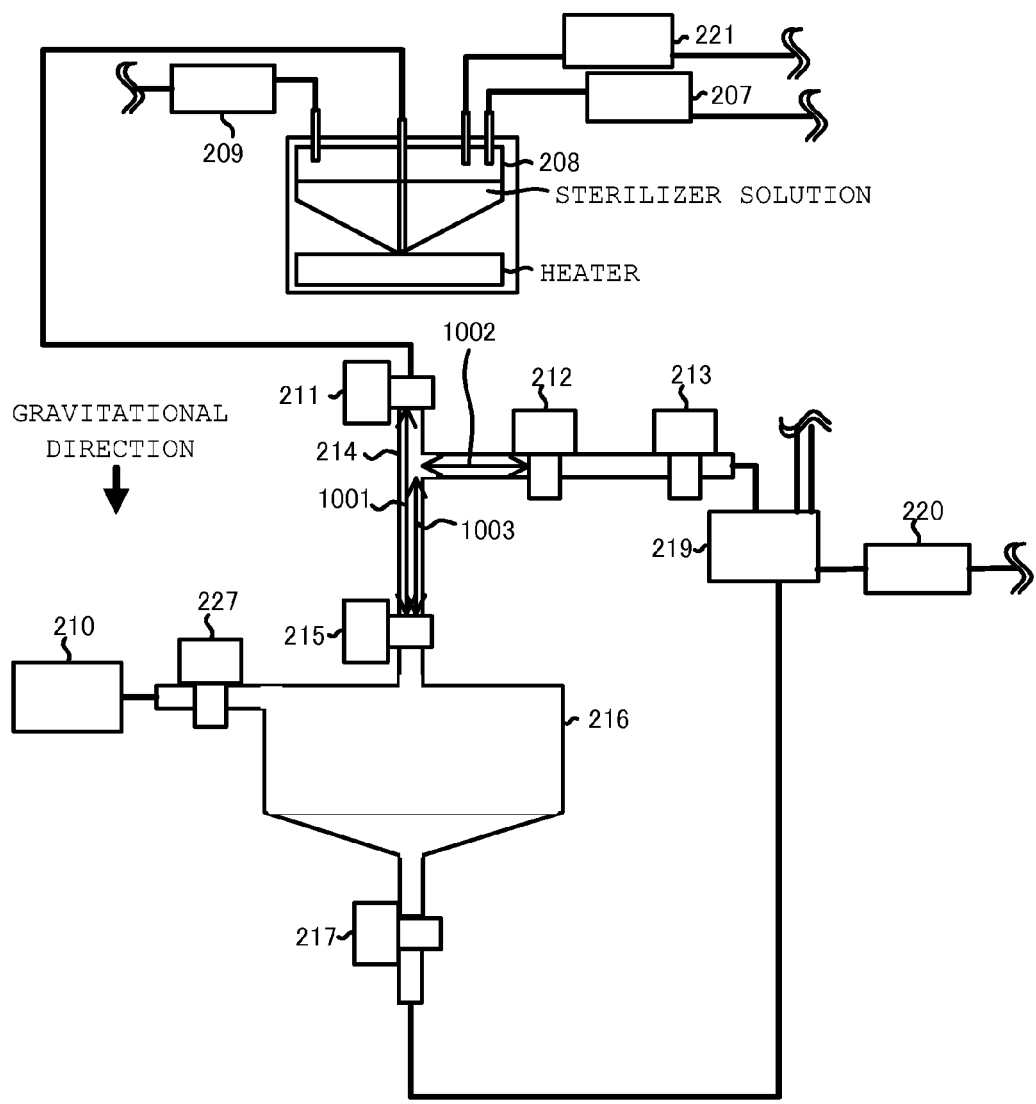
FIG. 10 is a block diagram illustrating an example a hardware configuration of a concentration furnace 208, a valve (V1) 211, a valve (V3) 212, a valve (V4) 213, a measuring pipe 214, a valve (V2) 215, a vaporizing furnace 216, a valve (V5) 217, and a valve (V9) 227 of the sterilization apparatus 100 according to an exemplary embodiment.

FIG. 10 is a block diagram illustrating an example of a hardware configuration of a concentration furnace 208, a valve (V1) 211, a valve (V3) 212, a valve (V4) 213, a measuring pipe 214, a valve (V2) 215, a vaporizing furnace 216, a valve (V5) 217, and a valve (V9) 227 of the sterilization apparatus 100 according to the present exemplary embodiment. The hardware blocks of FIG. 10, which are the same as the hardware illustrated in FIG. 2, are denoted by the same reference numerals.

In steps S704 and S729, the sterilization apparatus 100 operates the liquid feeding rotary pump 207 and suctions a predetermined amount (for example, 2 millimeters) of sterilizer in the cartridge 205, and introduces the predetermine amount of suctioned sterilizer into the concentration furnace 208.

In operation S706, as illustrated in FIG. 10, a heater is disposed at a lower portion of the concentration furnace 208, and the sterilizer is heated by the heat of the heater. When the sterilizer is hydrogen peroxide solution, water is vaporized by the heat of the heater. Further, the vaporized water is forced out to a conduit communicated with the gas exhausting HEPA filter 221 by the air carried through a conduct from the gas feeding pressing pump 209, and is exhausted from the concentration furnace 208. Accordingly, the sterilizer (a hydrogen peroxide solution) is concentrated.

As described referring to FIG. 7, in operation S710, the sterilizer in the concentration furnace 208 is introduced into the measuring pipe 214. As illustrated in FIG. 10, the measuring pipe 214 includes a straight pipe portion 1001 and a branch pipe portion 1002. The straight pipe portion 1001 is a linear pipe-shaped portion. The pipe of the straight pipe portion 1001 is disposed in a gravitational direction. Further, the branch pipe portion 1002 is a pipe-shaped portion extending from a middle portion or an upper portion of the straight pipe portion 1001 in a branch shape.

The straight pipe portion 1001 is disposed so that an axial center of the straight pipe portion and an axial center of the branch pipe portion 1002 are perpendicular to each other.

With this configuration, the sterilizer introduced from the concentration furnace 208 is configured to be stored in the straight pipe portion 1001 in the measuring pipe 214. The portion where the sterilizer is stored in the straight pipe portion 1001 is also called a sterilizer storage unit 1003. That is, the sterilizer storage unit 1003 has a sufficient space into which the sterilizer introduced from the concentration furnace 208 is stored.

For this reason, the sterilizer introduced from the concentration furnace 208 is stored in the sterilizer storage unit 1003, and the air introduced from the concentration furnace 208 together with the sterilizer is filled in a space other than the space for the sterilizer stored in the sterilizer storage unit 1003. That is, the space other than the space for the sterilizer is stored is a space communicated with the space in the branch pipe portion 1002, and thus the air is suctioned into the sterilization chamber 219 by opening the valve (V3) 212 and the valve (V4) 213 in operation S711.

Further, by opening the valve (V2) in operation S714, the sterilizer stored in the sterilizer storage unit 1003 is suctioned into the vaporizing furnace 216 to be vaporized. As illustrated in FIG. 10, as the liquid sterilizer is introduced into the vaporizing furnace 216 from the upper side of the vaporizing furnace 216, the sterilizer may be easily vaporized.

Further, as illustrated in FIG. 10, a conduit between the gas suctioning HEPA filter 210 and the vaporizing furnace 216 is disposed at an upper portion of the vaporizing furnace 216. For this reason, when the valve V9 is opened in operation S719, air (an exterior gas) is discharged from an upper portion of the vaporizing furnace 216 to the sterilization chamber 219 located at a lower portion of the vaporizing furnace 216, and thus the sterilizer adhered to the interior of the vaporizing furnace 216 and the vaporized sterilizer in the vaporizing furnace 216 may be easily removed widely, and more removed sterilizer may flow into the sterilization chamber 219.

A sterilization apparatus according to a second exemplary embodiment will be described with reference to FIGS. 12 and 13. In the second exemplary embodiment, parts different from the sterilization apparatus described in the first exemplary embodiment will be mainly described.

Figure 12:
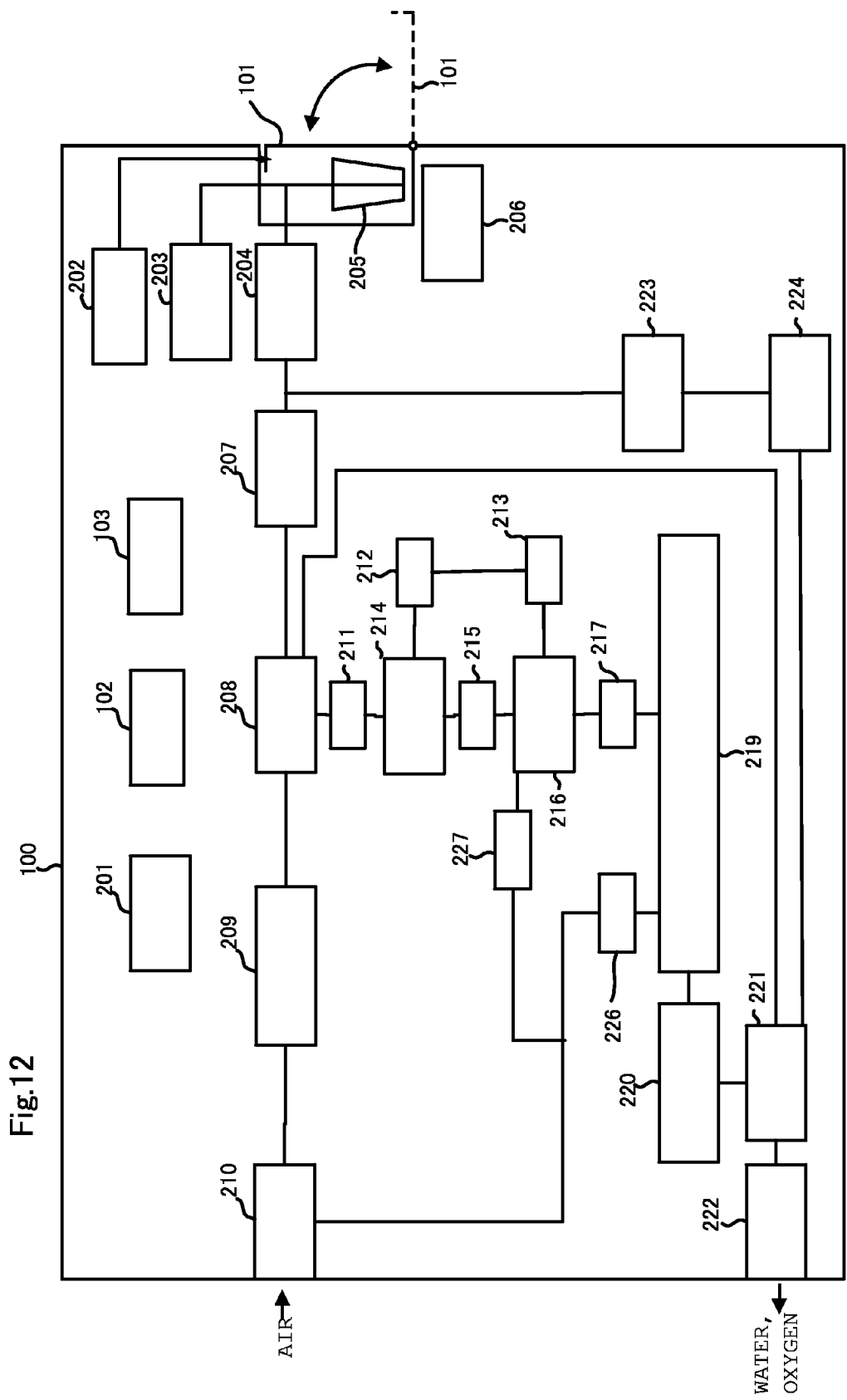
FIG. 12 is a block diagram illustrating an example of a hardware configuration of the sterilization apparatus according to an exemplary embodiment.

FIG. 12 is a block diagram illustrating an example of a hardware configuration of a sterilization apparatus according to the present exemplary embodiment. Further, FIG. 13 is a block diagram illustrating an example of a hardware configuration of a concentration furnace 208, a valve (V1) 211, a valve (V3) 212, a valve (V4) 213, a measuring pipe 214, a valve (V2) 215, a vaporizing furnace 216, a valve (V5) 217, and a valve (V9) 227 of the sterilization apparatus 100 according to the present exemplary embodiment.

Although a conduit directly communicated with the measuring pipe 214 and the sterilization chamber 219 is disposed in the sterilization apparatus 100 described in the first exemplary embodiment, a conduit directly communicated with the measuring pipe 214 and the sterilization chamber 219 is not provided in the second exemplary embodiment. For this reason, as illustrated in FIG. 12, the sterilization apparatus 100 of the second exemplary embodiment additionally employs a conduit communicated with the measuring pipe 214 and the vaporizing furnace 216.

That is, although, in the first exemplary embodiment, air may be prevented from being introduced into the sterilization chamber 219 when the vaporized sterilizer is injected into the sterilization chamber 219 by suctioning out the air stored in the measuring pipe 214 to the sterilization chamber 219 through a conduit directly communicated with the measuring pipe 214 and the sterilization chamber 219 In the second exemplary embodiment, the air may be prevented from being introduced into the sterilization chamber 219 when the vaporized sterilizer is injected into the sterilization chamber 219, by additionally providing a conduit communicated with the measuring pipe 214 and the vaporizing furnace 216 instead of the conduit and suctioning out the air stored in the measuring pipe 214 through the conduit to the vaporizing furnace 216.

The valve (V3) 212 and the valve (V4) 213 are disposed in a conduit communicated with the measuring pipe 214 and the vaporizing furnace 216, which is additionally provided in the second exemplary embodiment.

The valve (V3) 212 is a valve disposed in a conduit between the measuring pipe 214 and the vaporizing furnace 216, and is a valve configured in such a manner that when the valve is opened, the measuring pipe 214 and the vaporizing furnace 216 are communicated with each other through the conduit, and when the valve is closed, the measuring pipe 214 and the vaporizing furnace 216 are prevented from being communicated with each other through the conduit. Further, the valve is disposed around the measuring pipe 214, and is disposed at a location closer to the measuring pipe 214 than at least the below-described valve V4.

The valve (V4) 213 is a valve disposed in a conduit between the measuring pipe 214 and the vaporizing furnace 216, and is a valve configured in such a manner that when the valve is opened, the measuring pipe 214 and the vaporizing furnace 216 are communicated with each other through the conduit, and when the valve is closed, the measuring pipe 214 and the vaporizing furnace 216 are prevented from being communicated with each other through the conduit. Further, the valve is disposed around the vaporizing furnace 216, and is disposed at a location closer to the vaporizing furnace 216 than at least the below-described valve V3.

In the present exemplary embodiment, the measuring pipe 214 and the vaporizing furnace 216 are allowed to be communicated or prevented from being communicated with each other through the conduit by opening and closing the valve (V4) 213 and the valve (V3) 212. However, as in the first exemplary embodiment, the measuring pipe and the vaporizing furnace may be allowed to be communicated or prevented from being communicated with each other through the conduit by opening and closing any one of the valve (V4) 213 and the valve (V3) 212.

The sterilization apparatus 100 according to the second exemplary embodiment is the same as the sterilization apparatus 100 according to the first exemplary embodiment except for the above-described configurations, and a description thereof will be omitted.

The measuring pipe 214 is communicated with the concentration furnace 208 and the vaporizing furnace 216 through a conduit therebetween, respectively. Further, as illustrated in FIG. 12, the measuring pipe 214 and the vaporizing furnace 216 are communicated with each other through two conduits. One of the two conduits is disposed between the straight pipe portion 1001 of the measuring pipe 214 and the vaporizing furnace 216 as illustrated in FIG. 13, and the other one is disposed between the branch pipe portion 1002 of the measuring pipe 214 and the vaporizing furnace 216 as illustrated in FIG. 13.

The measuring pipe 214 is a pipe for opening the valve (V1) 211 to introduce the sterilizer from the concentration furnace 208 and opening the valve (V3) 212 and the valve (V4) 214 to remove unnecessary air suctioned from the cartridge 205 and/or unnecessary air introduced from the concentration furnace 208 through the measuring pipe 214. Details of the measuring pipe 214 will be described below with reference to FIG. 13.

A hardware block configuration of the concentration furnace 208, the valve (V1) 211, the valve (V3) 212, the valve (V4) 213, the measuring pipe 214, the valve (V2) 215, the vaporizing furnace 216, the valve (V5) 217, the valve (V9) 227, the valve (V7) 226, and the sterilization chamber 219 of the sterilization apparatus 100 according to the second exemplary embodiment will be described with reference to FIG. 13.

Figure 13:
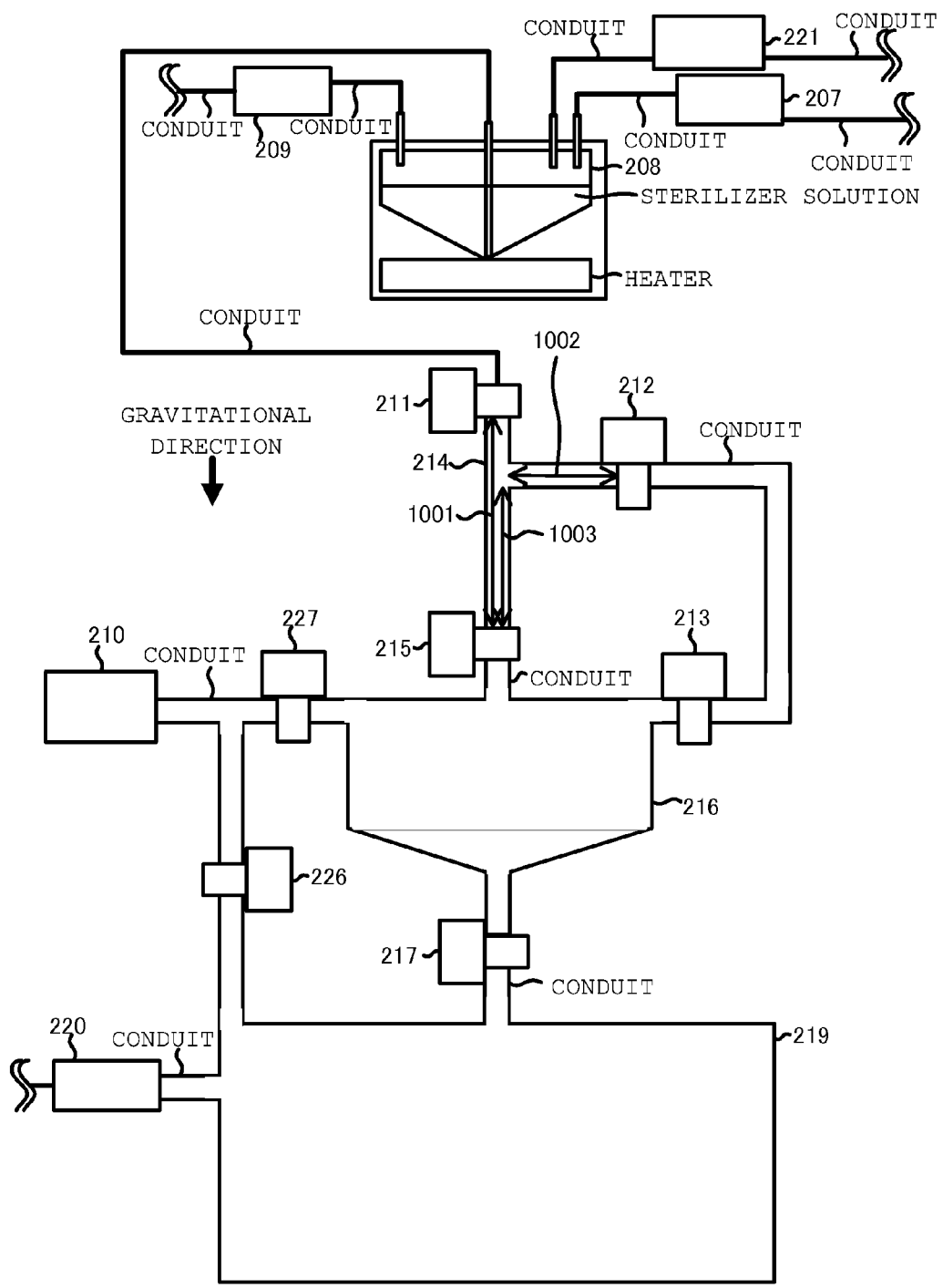
FIG. 13 is a block diagram illustrating an example of a hardware configuration of a concentration furnace 208, a valve (V1) 211, a valve (V3) 212, a valve (V4) 213, a measuring pipe 214, a valve (V2) 215, a vaporizing furnace 216, a valve (V5) 217 and a valve (V9) 227 of the sterilization apparatus 100 according to an exemplary embodiment.

FIG. 13 is a block diagram illustrating an example of a hardware configuration of the concentration furnace 208, the valve (V1) 211, the valve (V3) 212, the valve (V4) 213, the measuring pipe 214, the valve (V2) 215, the vaporizing furnace 216, the valve (V5) 217, the valve (V9) 227, the valve (V7) 226, and the sterilization chamber 219 of the sterilization apparatus 100 according to the present exemplary embodiment.

The hardware blocks illustrated in FIG. 13 which are the same as those illustrated in FIG. 12 are denoted by the same reference numerals.

In steps S704 and S729, the sterilization apparatus 100 operates the liquid feeding rotary pump 207 and suctions a predetermined amount (for example, 2 millimeters) of sterilizer in the cartridge 205, and introduces the predetermine amount of suctioned sterilizer into the concentration furnace 208.

In operation S706, as illustrated in FIG. 10, a heater is disposed at a lower portion of the concentration furnace 208, and the sterilizer is heated by the heat of the heater. When the sterilizer is hydrogen peroxide solution, water is vaporized by the heat of the heater. Further, the vaporized water is forced out to a conduit communicated with the gas exhausting HEPA filter 221 by the air carried through a conduit from the gas feeding pressing pump 209, and is exhausted from the concentration furnace 208. Accordingly, the sterilizer (a hydrogen peroxide solution) is concentrated.

As described referring to FIG. 7, in operation S710, the sterilizer in the concentration furnace 208 is introduced into the measuring pipe 214. As illustrated in FIG. 10, the measuring pipe 214 includes a straight pipe portion 1001 and a branch pipe portion 1002.

The straight pipe portion 1001 is a linear pipe-shaped portion. The pipe of the straight pipe portion 1001 is disposed in a gravitational direction. Further, the branch pipe portion 1002 is a pipe-shaped portion extending from a middle portion or an upper portion of the straight pipe portion 1001 in a branch shape. The straight pipe portion 1001 is disposed in such a manner that an axial center of the straight pipe portion and an axial center of the branch pipe portion 1002 are perpendicular to each other.

With this configuration, the sterilizer introduced from the concentration furnace 208 is stored in the straight pipe portion 1001 in the measuring pipe 214. The portion where the sterilizer is stored in the straight pipe portion 1001 is called a sterilizer storage unit 1003. That is, the sterilizer storage unit 1003 has a sufficient space into which the sterilizer introduced from the concentration furnace 208 is introduced.

For this reason, the sterilizer introduced from the concentration furnace 208 is stored in the sterilizer storage unit 1003, and the air introduced from the concentration furnace 208 together with the sterilizer is filled in a space other than the space for the sterilizer stored in the sterilizer storage unit 1003. That is, the space other than the space for the sterilizer is stored is a space communicated with the space in the branch pipe portion 1002, and thus the air is suctioned into the vaporizing furnace 216 by opening the valve (V3) 212 and the valve (V4) 213 in operation S711.

Further, by opening the valve (V2) in operation S714, the sterilizer stored in the sterilizer storage unit 1003 is suctioned into the vaporizing furnace 216 to be vaporized. As illustrated in FIG. 13, since the liquid sterilizer is introduced into the vaporizing furnace 216 from the upper side of the vaporizing furnace 216, the sterilizer may be easily vaporized.

Further, in operation S717, if the valve (V5) 217 is opened, the sterilizer in the vaporizing furnace 216 is diffused into the sterilization chamber 219 to sterilize a sterilization target present in the sterilization chamber 219.

Further, as illustrated in FIG. 13, a conduit between the gas suctioning HEPA filter 210 and the vaporizing furnace 216 is disposed at an upper portion of the vaporizing furnace 216. For this reason, when the valve (V9) is opened in operation S719, air (an exterior gas) is discharged from an upper portion of the vaporizing furnace 216 to the sterilization chamber 219 located at a lower portion of the vaporizing furnace 216, and thus the sterilizer adhered to the interior of the vaporizing furnace 216 and the vaporized sterilizer in the vaporizing furnace 216 may be easily removed widely, and a more amount of removed sterilizer may flow into the sterilization chamber 219.

Further, as illustrated in FIG. 13, a valve (V7) 226 is disposed in a conduit between the gas suctioning HEPA filter 210 and the sterilization chamber 219.

As described above, according to the present exemplary embodiment, by providing a mechanism for removing air introduced together with the sterilizer into a chamber of a process before introducing the sterilizer into the sterilization chamber, the air is prevented from being introduced into the sterilization chamber and a sterilizing action may be enhanced.

In this way, a structure for preventing air from being introduced into the sterilization chamber may be provided, and a sterilizing operation may be prevented from being lowered.

While the present exemplary embodiment has been described with reference to exemplary embodiments, it is to be understood that the disclosure is not limited to the disclosed exemplary embodiments. The scope of the following claims is to be accorded the broadest interpretation so as to encompass all modifications, equivalent structures, and functions.

This application claims priority from Japanese Patent Application No. 2011-222382 filed Oct. 6, 2011 and No. 2011-239562 filed Oct. 31, 2011, which is hereby incorporated by reference herein in its entirety.

What is claimed is:

1. A sterilization apparatus for sterilizing, using sterilizer, an object in a sterilization chamber, comprising:
   a direct conduit portion including a sterilizer pooling portion configured to pool sterilizer to be introduced;
   a first conduit extending from the direct conduit portion to the sterilization chamber and configured to pass air contained in the direct conduit portion to the sterilization chamber while leaving the sterilizer pooled in the sterilizer pooling;

the sterilization chamber configured to sterilize the object using gasified sterilizer obtained by vaporizing the sterilizer pooled in the sterilizer pooling portion;

a first valve attached to the first conduit between the direct conduit portion and the sterilization chamber to control passing the air contained in the direct conduit portion to the sterilization chamber; and a vacuuming device configured to vacuum the sterilization chamber, wherein the sterilization apparatus, by opening and closing the first valve before introducing the sterilizer into the sterilization chamber, sucks, through the first conduit, the air contained in the direct conduit portion into the sterilization chamber which has been vacuumed by the vacuuming device while leaving the sterilizer pooled in the sterilizer pooling portion as it is, and performs vacuuming of the sterilization chamber using the vacuuming device.

2. The sterilization apparatus according to claim 1, wherein the sterilization apparatus, by keeping the first valve open for a predetermined time and closing the first valve before introducing the sterilizer into the sterilization chamber, sucks, through the first conduit, the air contained in the direct conduit portion into the sterilization chamber which has been vacuumed by the vacuuming device while leaving the sterilizer pooled in the sterilizer pooling portion as it is, and performs vacuuming of the sterilization chamber using the vacuuming device.

3. The sterilization apparatus according to claim 2, further comprising:

a concentration chamber configured to concentrate the sterilizer;

a vaporizing chamber configured to vaporize the sterilizer; and a second valve configured to be opened and closed to control communication between the vaporizing chamber and the sterilizer pooling portion, wherein after the sterilizer is introduced from the concentration chamber into the sterilizer pooling portion, gas contained in the measuring pipe is removed by opening the first valve for a predetermined time and closing the first valve, and then opening the second valve.

4. A sterilization method in a sterilization apparatus for sterilizing an object including a concentration chamber configured to concentrate a sterilizer, a vaporizing chamber configured to vaporize the sterilizer, a measuring pipe into which the sterilizer is introduced from the concentration chamber before introduced into the vaporizing chamber, a vacuuming device configured to vacuum the sterilization chamber, and a first valve configured to be opened and closed to control communication between the sterilization chamber and the measuring pipe, the method comprising:

removing gas contained in the measuring pipe from the measuring pipe by opening the first valve, after the sterilizer is introduced from the concentration chamber into the measuring pipe.

5. The sterilization method according to claim 4, wherein in the removing the gas contained in the measuring pipe is removed from the measuring pipe by opening the first valve for a predetermined time, after the sterilizer is introduced from the concentration chamber into the measuring pipe.

6. The sterilization method according to claim 5, wherein the sterilization apparatus further includes a second valve configured to be opened and closed to control communication between the vaporizing chamber and the measuring pipe; and wherein, in the removing, the gas contained in the measuring pipe is removed by opening the first valve for a predetermined time and closing the first valve, and then opening the second valve, after the sterilizer is introduced from the concentration chamber into the measuring pipe.

7. The sterilization apparatus according to claim 1, further comprising:

a vaporizing chamber configured to vaporize the sterilizer pooled in the sterilizer pooling portion;

a second conduit through which the sterilizer pooling portion and the vaporizing chamber are communicated with each other; and a second valve provided to the second conduit through which the sterilizer pooling portion and the vaporizing chamber are communicated with each other, wherein the conduit configured to pass air contained in the direct conduit portion while leaving the sterilizer pooled in the sterilizer pooling portion as it is and being provided to the direct conduit portion is the first conduit through which the direct conduit portion and the sterilization chamber are communicated with each other;

wherein the sterilization chamber sterilizes the object using the gasified sterilizer obtained by vaporizing the sterilizer in the vaporizing chamber, and wherein the sterilization apparatus, by opening and closing the first valve before introducing the sterilizer pooled in the sterilizer pooling portion into the vaporizing chamber through the second conduit through which the sterilizer pooling portion and the vaporizing chamber are communicated with each other by opening the second valve, sucks, through the first conduit through which the direct conduit portion and the sterilization chamber are communicated with each other, the air contained in the direct conduit portion into the sterilization chamber which has been vacuumed by the vacuuming device while leaving the sterilizer pooled in the sterilizer pooling portion as it is, and performs vacuuming of the sterilization chamber using the vacuuming device.

8. The sterilization apparatus according to claim 7, further comprising:

a third conduit through which the vaporizing chamber and the sterilization chamber are communicated with each other; and a third valve provided to the third conduit through which the vaporizing chamber and the sterilization chamber are communicated with each other, wherein the sterilization apparatus, by opening and closing the first valve, sucks, through the first conduit through which the direct conduit portion and the sterilization chamber are communicated with each other, the air contained in the direct conduit portion into the sterilization chamber which has been vacuumed by the vacuuming device, by opening the second valve after sucking the air contained in the direct conduit portion into the sterilization chamber, introduces the sterilizer pooled in the sterilizer pooling portion into the vaporizing chamber through the second conduit through which the sterilizer pooling portion and the vaporizing chamber are communicated with each other and, by opening the third valve, introduces the gasified sterilizer obtained by vaporizing the sterilizer by the vaporizing chamber, and wherein the vacuuming device vacuums the sterilization chamber during the period prior to the gasified sterilizer obtained by vaporizing the sterilizer by the vaporizing chamber being introduced into the sterilization chamber by opening the third valve after the air contained in the direct conduit portion is sucked into the sterilization chamber by opening and closing the first valve.

9. The sterilization apparatus according to claim 1, further comprising:
a vaporizing chamber configured to vaporize the sterilizer pooled in the sterilizer pooling portion,
wherein the sterilization chamber sterilizes the object using the gasified sterilizer obtained by vaporizing the sterilizer pooled in the sterilizer pooling;
wherein the conduit configured to pass air contained in the direct conduit portion while leaving the sterilizer pooled in the sterilizer pooling portion as it is and being provided to the direct conduit portion is the first conduit through which the direct conduit portion and the vaporizing chamber are communicated with each other;
wherein the sterilization apparatus, by opening and closing the first valve before introducing the sterilizer pooled in the sterilizer pooling portion into the vaporizing chamber, sucks the air contained in the direct conduit portion into the vaporizing chamber decompressed by being communicated with the sterilization chamber which has been vacuumed by the vacuuming device, and
wherein the vacuuming devices performs, during the period from when the air contained in the direct conduit portion is sucked into the vaporizing chamber to when the sterilizer pooled in the sterilizer pooling chamber is introduced into the vaporizing chamber, the vacuuming in a state in which the sterilization chamber and the vaporizing chamber are communicated with each other.

10. The sterilization apparatus according to claim 1, further comprising a concentration chamber configured to concentrate the sterilizer,
wherein the direct conduit portion is a portion into which air, together with the sterilizer, is introduced via the concentration chamber, and
wherein the sterilizer pooling portion is a portion in which the sterilizer introduced into the direct conduit portion through the concentration chamber is pooled.

* * * * *